US008013187B2

(12) United States Patent
Kim et al.

(10) Patent No.: US 8,013,187 B2
(45) Date of Patent: Sep. 6, 2011

(54) 2-CYCLOPENTEN-1-ONE OXIME DERIVATIVES INHIBITING PRODUCTION OF TNF-α

(75) Inventors: Yeonjoon Kim, Yongin-si (KR); Sun-Young Kim, Seoul (KR); Jung Sun Hwang, Yongin-si (KR); Kyoung Min Lim, Suwon-si (KR); Miyoung Park, Anyang-si (KR); Hyun Ju Koh, Gunpo-si (KR); Sa-Yong Hong, Seoul (KR); Song Seok Shin, Yongin-si (KR); Jin Kyu Choi, Suwon-si (KR); Joo-Hyun Moh, Yongin-si (KR); Shin Chung, Yongin-si (KR); Byoung Young Woo, Yongin-si (KR); Sung Il Kim, Yangju-si (KR)

(73) Assignee: Amorepacific Corporation, Seoul (KR)

( * ) Notice: Subject to any disclaimer, the term of this patent is extended or adjusted under 35 U.S.C. 154(b) by 790 days.

(21) Appl. No.: 11/720,081

(22) PCT Filed: Nov. 30, 2005

(86) PCT No.: PCT/KR2005/004061
§ 371 (c)(1),
(2), (4) Date: Feb. 11, 2008

(87) PCT Pub. No.: WO2006/059867
PCT Pub. Date: Jun. 8, 2006

(65) Prior Publication Data
US 2009/0036501 A1    Feb. 5, 2009

(30) Foreign Application Priority Data
Dec. 2, 2004  (KR) .................. 10-2004-0100419

(51) Int. Cl.
*C07C 259/00*  (2006.01)
*C07D 305/00*  (2006.01)
*C07D 307/02*  (2006.01)
*C07D 339/08*  (2006.01)
*A01N 43/38*  (2006.01)
*A01N 43/08*  (2006.01)
*A01N 43/02*  (2006.01)

(52) U.S. Cl. .......... 564/265; 549/17; 549/491; 549/505; 514/415; 514/434; 514/461; 514/640

(58) Field of Classification Search .............. 549/505, 549/491, 17; 514/415, 640, 461, 434; 564/265
See application file for complete search history.

(56) References Cited

U.S. PATENT DOCUMENTS

| 5,631,286 A | 5/1997 | Christensen, IV et al. |
| 5,693,659 A | 12/1997 | Head et al. |
| 5,792,882 A | 8/1998 | Kawai et al. |

OTHER PUBLICATIONS

Hcaplus 2005:37302, "Phosphodiesterase-4 (PDE4) as a target for anti-inflammatory drug discovery: Current status and future direction", Wang et. al., 2003.*
Hcaplus 1998:370703, "Revisiting the role of tumor necrosis factor alpha and the response to surgical injury and inflammation", Ksontini et. al., 1998.*
Hcaplus 2004:434786 abstract, "Targeting tumor necrosis factor-alpha in the therapy of psoriasis", Gisondi et. al., 2004.*
Palladino, M. Nat. Rev. Drug. Discov., vol. 2, 2003, pp. 736-746.*
Newton, R.C., et al., "Therapeutic Potential and Strategies for Inhibiting Tumor Necrosis Factor-α," J. of Medicinal Chemistry, 42(13): 2295-2314 (1999).
Burnour, C., et al., "Recent Advances in PDE4 Inhibitors as Immunoregulators and Anti-Inflammatory Drugs," Curr. Pharm. Design, 81255-1296 (2002).
Sullivan, G.W., "Role of $A_{2,4}$Adenosine Receptors in Inflammation," Drug Devel. Res., 45:103-112 (1998.
Burke, J.R., et al., "BMS-345541 Is a Highly Selective Inhibitor of IκB Kinase That Binds at an Allosteric Site of the Enzyme and Blocks NF-κB-dependent Transcription in Mice," J. Biol. Chem., 278, 3: 1450-1456 (2003).
McHung, S.M., et al., "Thalidomide and derivatives immunological investigations of tumour necrosis factor-alpha (TNF-α) inhibition suggest drugs capable of selective gene regulation," Clin. Exp. Immunol, 110: 151-154 (1997).
Gale, J.D., et al., "Emerging Opportunities for the Treatment of Inflammatory Bowel Disease," Ann. Rep. Med. Chem., 38: 141-152 (2003).

* cited by examiner

Primary Examiner — Janet Andres
Assistant Examiner — Heidi Reese
(74) Attorney, Agent, or Firm — Sughrue Mion, PLLC

(57) ABSTRACT

2-cyclopenten-1-one oxime derivatives represented by Formula (I), or pharmaceutically acceptable salts thereof inhibit the production of TNF-α or PDE4, and therefore show therapeutic effect in inflammatory or immunological disorders mediated through TNF-α or PDE4.

10 Claims, No Drawings

2-CYCLOPENTEN-1-ONE OXIME DERIVATIVES INHIBITING PRODUCTION OF TNF-α

FIELD OF INVENTION

The present invention relates to a class of compounds that potently inhibit in vivo and in vitro production of TNF-α. Also this invention relates to the therapeutic utility of such compounds or pharmaceutically acceptable salts thereof in inflammatory and immunological disorders mediated through TNF-α.

BACKGROUND OF THE INVENTION

Tumor necrosis factor-alpha (TNF-α) is a pro-inflammatory cytokine discovered decades ago. TNF-α is produced by diverse types of cells in response to inflammatory and immunological stimuli. [*Trends Cell. Biol.* vol 5, 392-399 (1995)] For example, monocytes treated with lipopolysaccharide (LPS) significantly increases the production of TNF-α. Although TNF-α was also known to shrink tumors through apoptosis, it plays a central role in inflammation and immunology.

Abundant presence of TNF-α has been observed in a variety of immunological disorders including but not limited to rheumatoid arthritis, psoriasis, eczema, Crohn's disease, chronic obstructive pulmonary disease (COPD), systemic lupus erythematosus (SLE), sepsis, endotoxin shock, multiple sclerosis, chronic hepatitis, and so on. [*J. Med. Chem.* vol 42, 2295-2314 (1999); *Am. J. Respir. Crit. Care Med.* vol 153, 633-637 (1996); *Lupus* vol 11, 102-108 (2002); *Hepato-gastroenterology*. vol 47, 1675-1679 (2000)]

Blockade or neutralization of the TNF-α activity by a TNF-α monoclonal antibody has been found effective in treating immunological disorders including but not limited to rheumatoid arthritis, ankylosing spondylitis, Crohn's disease and psoriatic arthritis, as seen with the cases of infliximab (Remicade™) and adalimumab (Humira™). [Remicade™ (infliximab) Prescribing Information. Centocor Inc. September 2005; Humira™ (adalimumab) Prescribing Information. Abbott Lab October 2005.] Etanercept (Enbrel™) is a fusion protein with the decoy receptor part for TNF-α and therefore neutralizes the biological activity of TNF-α. Etanercept is indicated for rheumatoid arthritis, ankylosing spondylitis, psoriasis, and psoriatic arthritis in the US. [Enbrel™ (etanercept) Prescribing Information. Immunex Corporation. July 2005.] These protein drugs are currently available by injectable formulations only.

To date many biological targets are known to inhibit the cellular production of TNF-α. Pro-TNF-α is cleaved into the active soluble form of TNF-α by TNF-α converting enzyme (TACE). [*Nature* vol 385, 729-733 (1997)] Production of TNF-α is decreased by an increase in the cytosolic level of cAMP. Since inhibition of phosphodiesterase 4 (PDE4) increases the cytosolic level of cAMP, PDE4 inhibitors, such as rolipram, cilomilast and roflumilast, attenuate the production of TNF-α. [*Curr. Pharm. Design* vol 8, 1255-1296 (2002)] Adenosine receptor $A_{2a}$ is coupled with adenylate cyclase and its agonists, such as CGS21680 and NECA, inhibit the synthesis of TNF-α. [*Drug Devel. Res.* vol 45, 103-112 (1998)] Kinases such as NIK, IKK, and PKB, which are involved in the signaling of NF-κB, are known to suppress the production of TNF-α if inhibited. IKK inhibitors such as BMS-345541 block phosphorylation on IκB and inhibit the NFκB-dependent transcription. [*J. Biol. Chem.* vol 278, 1450-1456 (2003)] 5-aminosalicylic acid is known to inhibit IKK at therapeutically relevant dose for inflammatory bowel disease (IBD). Aspirin, a traditional nonsteroidal anti-inflammatory drug, is also known to inhibit IKK at high dose level. [*Nature* vol 396, 77-80 (1998)] Inhibition of MAP kinases such as p38 and c-Jun N-terminal kinase (JNK) suppresses the TNF-α production. p38 inhibitors such as VX-745 and SB203580 inhibited TNF-α production in cells treated with LPS, and showed therapeutic effect in animal models for rheumatoid arthritis. [*Curr. Opin. Investig. Drugs* vol 5, 566-571 (2003)] Thalidomide is indicated for systemic lupus erythematosus (SLE), although thalidomide weakly inhibits the synthesis of TNF-α at cellular level. It appears that thalidomide destabilizes TNF-α mRNA to decrease the TNF-α production. [*Clin. Exp. Immunol.* vol 110, 151-154 (1997)] Steroids also potently inhibit production of TNF-α. [*J. Exp. Med.* vol 172, 391-394 (1990)]

Reflecting that TNF-α plays a central role in inflammation and immunology, agents inhibiting the biological activity or production of TNF-α are expected to show therapeutic effect in a variety of disorders such as rheumatoid arthritis, psoriasis, psoriatic arthritis, atopic dermatitis, inflammatory bowel disease including ulcerative colitis and Crohn's disease, ankylosing spondylitis, multiple sclerosis, systemic lupus erythematosus (SLE), chronic obstructive pulmonary disease (COPD), sepsis, endotoxin shock, hepatitis, Type I diabetes, and so on. Some types of agents were found more effective for some disorders than others, depending on the mode of action and their physiochemical properties. PDE4 inhibitors such as roflumilast and cilomilast, for example, have been heavily developed for COPD. On the other hand, anti-TNF-α biologics were initially indicated for rheumatoid arthritis, and their indications are expanding to include ankylosing spondylitis, psoriasis, and Crohn's disease. 5-aminosalicylic acid and sulfasalazine are used to treat moderate to mild inflammatory bowel disease, while steroids and anti-TNF-α biologics are indicated for severe cases. There have been attempts to treat inflammatory bowel disease using PDE4 inhibitors. [*Ann. Rev. Med. Chem.* vol 38, 141-152 (2003)] Although p38 inhibitors such as VX-702 were evaluated for human rheumatoid arthritis, their therapeutic utility remains to be established for MAP Kinase inhibitors. [*Curr. Opin. Drug Discov. Devel.* vol 8, 421-430 (2005)] Steroids are initially effective for diverse kinds of immunological disorders, however, their long term use is strongly limited due to adverse events.

Although anti-TNF-α biologics such as infliximab, adalimumab and etanercept are widely used to treat immunological disorders such as rheumatoid arthritis and psoriasis, these protein drugs are doomed to be expensive and administered by injection. In this regard, small molecules inhibiting the action or production of TNF-α are in strong demand due to cost and convenience of avoiding injection.

SUMMARY OF THE INVENTION

This invention provides embodiments relating to 2-cyclopenten-1-one oxime derivatives represented by Formula I, or pharmaceutically acceptable salts or compositions thereof, and their therapeutic effect in inflammatory and immunological disorders mediated through TNF-α or PDE4. The present invention also provides methods employed for the synthesis of such compounds of Formula I.

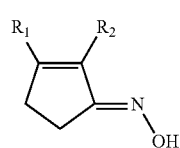

Formula I

In one embodiment of the present invention, compounds of Formula I are provided:
wherein,
$R_1$ represents a linear or branched $C_1$-$C_{10}$ alkyl group, or a $C_3$-$C_7$ cycloalkyl group; and $R_2$ represents an aromatic group with or without substituent(s).

In another embodiment of the present invention, compounds of Formula I are demonstrated to inhibit the production of TNF-α in cells stimulated to produce TNF-α. Also compounds of Formula I are demonstrated to potently inhibit isozymes of phosphodiesterase 4.

In yet another embodiment of the present invention, compounds of Formula I are demonstrated to inhibit in vivo production of TNF-α and to suppress inflammation or immunological responses in animal models.

Accordingly, compounds of Formula I are useful for prevention or treatment of inflammatory or immunological disorders mediated through TNF-α or PDE4. Examples of such disorders include rheumatoid arthritis, psoriasis, psoriatic arthritis, atopic dermatitis, inflammatory bowel disease including ulcerative colitis and Crohn's disease, ankylosing spondylitis, multiple sclerosis, systemic lupus erythematosus (SLE), chronic obstructive pulmonary disease (COPD), sepsis, endotoxin shock, hepatitis, Type I diabetes, and so on.

A compound of Formula I can be converted into a pharmaceutically-acceptable salt by neutralizing the compound, depending on the presence of an acidic group or a basic group in the compound, with an equivalent amount of an appropriate pharmaceutically-acceptable acid or base, such as potassium hydroxide, sodium hydroxide, hydrochloric acid, methansulfonic acid, citric acid, and the like. A compound of Formula I or a pharmaceutically-acceptable salt thereof can be administered along with pharmaceutically-acceptable adjuvant ingredients, including but not limited to, citric acid, sodium chloride, tartaric acid, stearic acid, starch, gelatin, talc, sesame oil, ascrobic acid, methylcellulose, sodium carboxymethylceluose, polyethyleneglycol (PEG), polypropyleneglycol, sweeteners, preservatives, water, ethanol, titanium oxide, sodium bicarbonate, silicified microcrystalline cellulose, soybean lecithin, and the like. A compound of Formula I or a pharmaceutically acceptable salt thereof can be formulated in a variety of dosage forms such as tablet, powder, granule, hard capsule, soft capsule, oral suspension, spray solution for inhalation, injectable solution, cream for topical application, transdermal patch, and the like. A compound of Formula I or a pharmaceutically-acceptable salt thereof can be administered to a human or animal subject at a daily dose of up to 100 mg/kg body weight but preferably up to 10 mg/kg body weight, depending on the indications, symptoms, or conditions of the subject.

In a preferred embodiment of the present invention, compounds of Formula I of interest are provided:
wherein,
$R_1$ represents a linear or branched $C_1$-$C_6$ alkyl, cyclopentyl, or cyclohexyl; and
$R_2$ represents an aromatic group with or without substituent(s), wherein the aromatic group is selected from phenyl, pyridyl, naphthyl, indolyl, thienyl, benzo[b]thienyl, dibenzofuranyl, or thianthrenyl.

In another preferred embodiment of the present invention, compounds of Formula I of strong interest are provided:
wherein,
$R_1$ represents a linear or branched $C_1$-$C_6$ alkyl, cyclopentyl, or cyclohexyl; and
$R_2$ represents an aromatic group selected from pyridyl, naphthyl, indolyl, thienyl, benzo[b]thienyl, dibenzofuranyl, or thianthrenyl; or $R_2$ represents a phenyl group with substituent(s) as provided below:

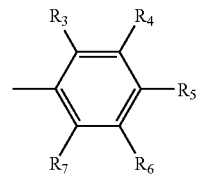

wherein, $R_3$ to $R_7$ are independently selected from hydrido, a linear or branched $C_1$-$C_9$ alkyl group, alkenyl, haloalkyl, aryl, halo, nitro, amino, alkylamino, alkylaminoalkyl, methylenedioxy, alkoxy, haloalkoxy, benzyloxy, alkylthio, alkylsulfonyl, alkylsulfinyl, cyano, carboxy, alkoxycarbonyl, alkoxyalkyl, hydroxy, hydroxyalkyl carbamoyl, N-hydroxy-iminoalkyl, or N—(N-hydroxy-iminoalkyl)amino.

In yet another preferred embodiment of the instant invention, specific compounds of Formula I of strong interest are the following group of compounds:
3-cyclopentyl-2-(4-fluorophenyl)-2-cyclopenten-1-one oxime;
3-cyclopentyl-2-(3,4-difluorophenyl)-2-cyclopenten-1-one oxime;
2-(3-chloro-4-fluorophenyl)-3-cyclopentyl-2-cyclopenten-1-one oxime;
3-cyclopentyl-2-(3-nitrophenyl)-2-cyclopenten-1-one oxime;
3-cyclopentyl-2-(4-methyl-3-nitrophenyl)-2-cyclopenten-1-one oxime;
3-cyclopentyl-2-(3,4-dimethoxyphenyl)-2-cyclopenten-1-one oxime;
3-cyclopentyl-2-(3-methoxyphenyl)-2-cyclopenten-1-one oxime;
3-cyclopentyl-2-{4-methoxy-3-(methoxymethyl)phenyl}-2-cyclopenten-1-one oxime;
2-{4-(benzyloxy)phenyl}-3-cyclopentyl-2-cyclopenten-1-one oxime;
3-cyclopentyl-2-(3,4-methylenedioxyphenyl)-2-cyclopenten-1-one oxime;
3-cyclopentyl-2-{3-(trifluoromethoxy)phenyl}-2-cyclopenten-1-one oxime;
2-(3-cyanophenyl)-3-cyclopentyl-2-cyclopenten-1-one oxime;
2-(3-cyano-4-fluorophenyl)-3-cyclopentyl-2-cyclopenten-1-one oxime;
3-cyclopenty-2-{3-(N,N-dimethylaminomethyl)phenyl}-2-cyclopenten-1-one oxime;
3-cyclopentyl-2-{3-(N,N-dimethylamino)phenyl}-2-cyclopenten-1-one oxime;
3-cyclopentyl-2-{5-(1H)-indolyl}-2-cyclopenten-1-one oxime;
3-cyclopentyl-2-(6-methoxynaphthyl)-2-cyclopenten-1-one oxime;
3-cyclopentyl-2-(4-vinylphenyl)-2-cyclopenten-1-one oxime;
3-cyclopentyl-2-(4-dibenzofuranyl)-2-cyclopenten-1-one oxime;
3-cyclopentyl-2-(2-thianthrenyl)-2-cyclopenten-1-one oxime;
3-cyclopentyl-2-(3-carbamoylphenyl)-2-cyclopenten-1-one oxime;
3-cyclopentyl-2-{3-(methylthio)phenyl}-2-cyclopenten-1-one oxime;

3-cyclopentyl-2-{3-(methylsulfonyl)phenyl}-2-cyclopenten-1-one oxime;
3-cyclopentyl-2-(3-hydroxyphenyl)-2-cyclopenten-1-one oxime;
3-cyclopentyl-2-{3-(hydroxymethyl)phenyl}-2-cyclopenten-1-one oxime;
3-cyclopentyl-2-{4-(hydroxymethyl)phenyl}-2-cyclopenten-1-one oxime;
3-cyclohexyl-2-(4-fluorophenyl)-2-cyclopenten-1-one oxime;
2-(3-chloro-4-fluorophenyl)-3-cyclohexyl-2-cyclopenten-1-one oxime;
3-cyclohexyl-2-(3-fluorophenyl)-2-cyclopenten-1-one oxime;
3-cyclohexyl-2-(3,4-difluorophenyl)-2-cyclopenten-1-one oxime;
3-cyclohexyl-2-(3-nitrophenyl)-2-cyclopenten-1-one oxime;
3-cyclohexyl-2-(3-methoxyphenyl)-2-cyclopenten-1-one oxime;
3-butyl-2-(4-fluorophenyl)-2-cyclopenten-1-one oxime;
3-butyl-2-(3,4-difluorophenyl)-2-cyclopenten-1-one oxime;
3-butyl-2-(2-fluorophenyl)-2-cyclopenten-1-one oxime;
3-butyl-2-(2,4-difluorophenyl)-2-cyclopenten-1-one oxime;
2-(3-bromophenyl)-3-butyl-2-cyclopenten-1-one oxime;
3-butyl-2-(3,4-dichlorophenyl)-2-cyclopenten-1-one oxime;
3-butyl-2-(3-nitrophenyl)-2-cyclopenten-1-one oxime;
3-butyl-2-(3-fluoro-4-methoxyphenyl)-2-cyclopenten-1-one oxime;
3-butyl-2-(3-fluoro-4-hydroxyphenyl)-2-cyclopenten-1-one oxime;
3-butyl-2-(3-ethoxyphenyl)-2-cyclopenten-1-one oxime;
3-butyl-2-(3,4-dimethoxyphenyl)-2-cyclopenten-1-one oxime;
3-butyl-2-(3-methoxyphenyl)-2-cyclopenten-1-one oxime;
3-butyl-2-(3,4-methylenedioxyphenyl)-2-cyclopenten-1-one oxime;
3-butyl-2-{4-(trifluoromethoxy)phenyl}-2-cyclopenten-1-one oxime;
3-butyl-2-{(3-(hydroxymethyl)phenyl}-2-cyclopenten-1-one oxime;
3-butyl-2-(3,4-dihydroxyphenyl)-2-cyclopenten-1-one oxime;
3-butyl-2-(3-hydroxyphenyl)-2-cyclopenten-1-one oxime;
2-(3-aminophenyl)-3-butyl-2-cyclopenten-1-one oxime;
3-butyl-2-{3-(ethoxycarbony)phenyl}-2-cyclopenten-1-one oxime;
3-butyl-2-(3-carboxyphenyl)-2-cyclopenten-1-one oxime;
3-butyl-2-(4-carboxyphenyl)-2-cyclopenten-1-one oxime;
3-butyl-2-(3,4-dimethylphenyl)-2-cyclopenten-1-one oxime;
3-butyl-2-(3-methylphenyl)-2-cyclopenten-1-one oxime;
3-butyl-2-(4-butylphenyl)-2-cyclopenten-1-one oxime;
3-butyl-2-(3-fluoro-4-phenylphenyl)-2-cyclopenten-1-one oxime;
3-butyl-2-{3-(trifluoromethyl)phenyl}-2-cyclopenten-1-one oxime;
3-butyl-2-{4-(methanesulfinyl)phenyl}-2-cyclopenten-1-one oxime;
3-butyl-2-{4-(methanesulfonyl)phenyl}-2-cyclopenten-1-one oxime;
3-butyl-2-{3-(N-hydroxyacetimidoyl)aminophenyl}-2-cyclopenten-1-one oxime;
3-butyl-2-{3-(1-N-hydroxyiminoethyl)phenyl}-2-cyclopenten-1-one oxime;
3-butyl-2-{3-(N-hydroxyiminomethyl)phenyl}-2-cyclopenten-1-one oxime;
2-(2-benzo[b]thienyl)-3-butyl-2-cyclopenten-1-one oxime;
3-pentyl-2-phenyl-2-cyclopenten-1-one oxime;
2-(4-fluorophenyl)-3-pentyl-2-cyclopenten-1-one oxime;
2-(3-fluorophenyl)-3-pentyl-2-cyclopenten-1-one oxime;
2-(3,4-difluorophenyl)-3-pentyl-2-cyclopenten-1-one oxime;
2-(3,5-difluorophenyl)-3-pentyl-2-cyclopenten-1-one oxime;
2-(3-chloro-4-fluorophenyl)-3-pentyl-2-cyclopenten-1-one oxime;
2-(3-nitrophenyl)-3-pentyl-2-cyclopenten-1-one oxime;
3-pentyl-2-(3,4,5-trimethoxyphenyl)-2-cyclopenten-1-one oxime;
2-(4-biphenyl)-3-pentyl-2-cyclopenten-1-one oxime;
3-pentyl-2-{4-(trifluoromethyl)phenyl}-2-cyclopenten-1-one oxime;
2-(1-naphthyl)-3-pentyl-2-cyclopenten-1-one oxime;
3-pentyl-2-(3-pyridyl)-2-cyclopenten-1-one oxime;
3-pentyl-2-(3-thienyl)-2-cyclopenten-1-one oxime;
2-(4-fluorophenyl)-3-propyl-2-cyclopenten-1-one oxime;
2-(3,4-difluorophenyl)-3-propyl-2-cyclopenten-1-one oxime;
2-(3-nitrophenyl)-3-propyl-2-cyclopenten-1-one oxime;
3-ethyl-2-(4-fluorophenyl)-2-cyclopenten-1-one oxime;
2-(3,4-difluorophenyl)-3-ethyl-2-cyclopenten-1-one oxime;
2-(4-fluorophenyl)-3-methyl-2-cyclopenten-1-one oxime;
2-(3,4-difluorophenyl)-3-methyl-2-cyclopenten-1-one oxime;
2-(4-fluorophenyl)-3-isobutyl-2-cyclopenten-1-one oxime;
2-(3,4-difluorophenyl)-3-isobutyl-2-cyclopenten-1-one oxime;
2-(3,4-methylenedioxyphenyl)-3-isobutyl-2-cyclopenten-1-one oxime;
3-isobutyl-2-(3-nitrophenyl)-2-cyclopenten-1-one oxime;
2-(3-cyanophenyl)-3-isobutyl-2-cyclopenten-1-one oxime;
2-(3-fluoro-4-n-nonylphenyl)-3-isobutyl-2-cyclopenten-1-one oxime; and
2-(3-butoxyphenyl)-3-isobutyl-2-cyclopenten-1-one oxime.

Terms and abbreviations used in this invention are illustrated in Table 1.

TABLE 1

Definition of the terms and abbreviations used in the present invention.

| Term or Abbreviation | Definition or Illustration |
| --- | --- |
| Alkyl | Linear or branched alkyl radical |
| Alkoxy | Oxy radical with an alkyl radical attached to. Examples are methoxy, ethoxy, iso-propyloxy, and the like. |
| Alkenyl | Alkyl radical with at least one carbon-carbon double bond therein |
| Alkoxyalkyl | Alkyl radical substituted with one alkoxy radical |
| Alkoxycarbonyl | "—C(O)—" substituted with one alkoxy radical |
| Alkylsulfinyl | "—S(O)—" substituted with one alkyl radical |
| Alkylsulfonyl | "—S(O)$_2$—" substituted with one alkyl radical |
| Alkylthio | "—S—" substituted with one alkyl radical |
| Aminoalkyl | Alkyl radical with one amino radical (NH$_2$) attached to |
| Carbamoyl | "—C(O)—NH$_2$" radical |
| Halo | Halogen atom such as F, Cl, Br, or I |
| Haloalkyl | Alkyl radical substituted with one or more halogen atom(s). Examples are fluoromethyl (F—CH$_2$—), 1-chloroethyl (CH$_3$—CHCl—), trifluoromethyl (CF$_3$—), and the like. |
| Hydrido | Single hydrogen atom |
| IFN-γ | Interferon gamma |
| N-Alkylamino | "—NH—" substituted with an alkyl radical. Examples are N-methylamino (CH$_3$—NH—), N-ethylamino (CH$_3$CH$_2$—NH—), and the like. |
| N-Hydroxyiminoalkyl | "—C(N—OH)—" substituted with hydrido or an alkyl radical |

TABLE 1-continued

Definition of the terms and abbreviations used in the present invention.

| Term or Abbreviation | Definition or Illustration |
| --- | --- |
| N—(N-hydroxy-iminoalkyl)amino | "—NH—" substituted with a (N-hydroxyiminoalkyl) radical |
| Formyl | "CHO—" radical |
| LPS | Lipopolysaccharide |
| Methylenedioxy | "—O—CH$_2$—O—" radical |
| PDE4 | Phosphodiesterase 4 |
| PBMC | Peripheral mononuclear cell |
| TNF-α | Tumor necrosis factor α |

Synthesis of Compounds of Formula I

Compounds of Formula I are prepared as summarized in scheme 1, in which $R_1$ and $R_2$ are as defined for Formula I. In some cases, there are minor modifications applied during executions of scheme 1, and these modifications are considered to be obvious to a skilled person and are provided where applicable.

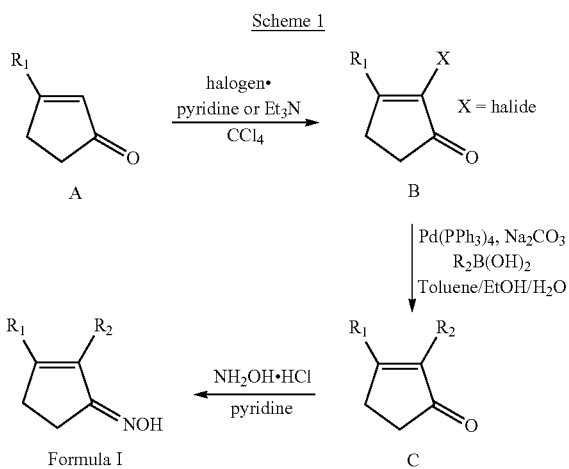

2-cyclopenten-1-one derivative A is halogenated by treatment of a halogen complex of either triethylamine or pyridine in carbon tetrachloride to yield 2-halo cyclopenten-1-one B. [*Tetrahedron Lett*. vol 33, 917-920 (1992)] Suzuki coupling of the halide compound with an aromatic boronic acid afforded the coupling product C, which is then condensed into a compound of Formula I by reacting with hydroxylamine hydrochloride in pyridine. [*Chem. Rev*. vol 95, 2457-2483 (1995)]

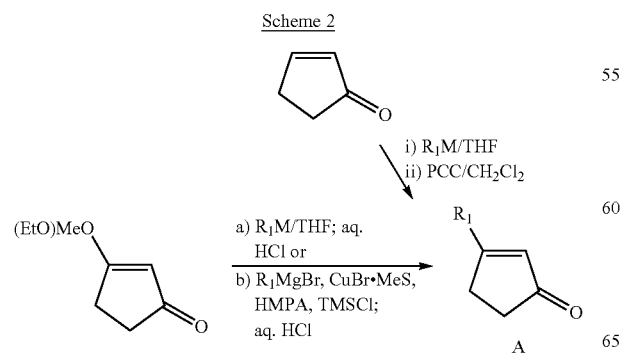

2-cyclopenten-1-one derivative A of scheme 1 is prepared by three different methods as described in scheme 2. In one method, an alkyl or cycloalkyl metal (M=Li, MgBr or MgCl) reagent is added to 2-cyclopenten-1-one, and the resulting allylic alcohol is subjected to oxidative rearrangement using pyridinium chlorochromate (PCC) to afford a 2-cyclopenten-1-one derivative A. [*Tetrahedron Lett*. vol 30, 1033-1036 (1989)] Another method is to react either 3-ethoxy-2-cyclopenten-1-one or 3-methoxy-2-cyclopenten-1-one with an alkyl or cycloalkylmetal (M=Li, MgBr or MgCl) reagent and to convert the resulting adduct to the 2-cyclopenten-1-one derivative A by treating with hydrochloric acid. [*J. Am. Chem. Soc*. vol 110, 4625-4633 (1988)] In the third method, 1,4-addition of an alkyl or cycloalkyl cuprate to the 3-alkoxy-2-cyclopenten-1-one is facilitated by trimethylsilyl chloride (TMSCl) in the presence of hexamethyl phosphoramide (HMPA), and the resulting adduct is converted to the 2-cyclopenten-1-one derivative A by treating with hydrochloric acid. [*Tetrahedron* vol 45, 349-362 (1989)]

Alternatively, compounds of Formula I are also prepared as described in scheme 3, where key intermediate cyclopenten-1-one derivative C is obtained by an intermolecular Pauson-Khand reaction between alkyne D and ethylene. [*Angew. Chem. Int. Ed*. vol 39, 636-638 (2000) and references therein] Alkyne D is synthesized by a palladium catalyzed coupling of alkyne and aryl halide. [*Chem. Rev*. vol 103, 1979-2017 (2003)] The Pauson-Khand reaction of alkyne D is effected under high pressure carbon monoxide and ethylene in the presence of a non-stoichiometric amount of dicobalt octacarbonyl and dimethylsulfoxide as a promoter. Cyclopentenone C is then converted to a compound of Formula I according to scheme 1.

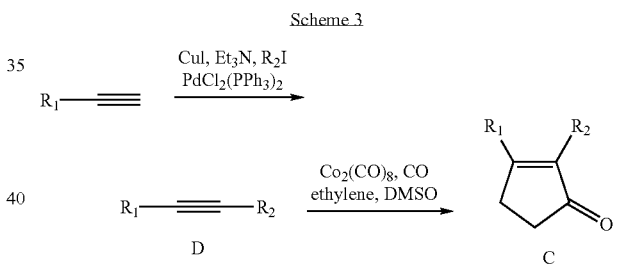

Although compounds of Formula I were prepared as follows, it is not intended to limit the scope of the compounds of this invention to the compounds provided below. These compounds should be rather taken as examples.

EXAMPLE 1

3-cyclopentyl-2-(4-fluorophenyl)-2-cyclopenten-1-one oxime

The titled compound was prepared according to the four step procedure as described below.

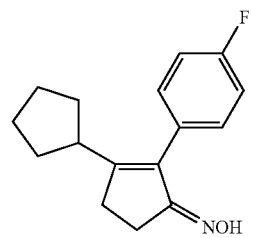

STEP 1 (Synthesis of 3-cyclopentyl-2-cyclopenten-1-one): To a stirred suspension of 800 mg copper bromide dimethylsulfide in 100 ml tetrahydrofuran (THF) equilibrated to −78° C., were added in series 24 ml 2.0 M cyclopentylmagnesium chloride in diethyl ether and 8 ml hexamethylphosphoramide (HMPA) under inert atmosphere. To the mixture was added a solution of 5.4 ml trimethylsilyl chloride (TMSCl) and 4.3 g 3-methoxy-2-cyclopenten-1-one in 20 ml THF. The reaction mixture was slowly warmed to room temperature and stirred for 3 hours, to which was added 50 ml 10% aqueous HCl. The resulting reaction mixture was stirred for another 10 min and subjected to extraction with ethyl acetate. The organic layer was washed with water and brine, dried over anhydrous magnesium sulfate, and filtered. Then the filtrate was concentrated under reduced pressure and purified by column chromatography (silica gel, hexane/ethyl acetate=3:1) to yield 4.5 g of 3-cyclopentyl-2-cyclopenten-1-one as an oil. $^1$H NMR (CDCl$_3$, 300 MHz): δ 5.94 (m, 1H), 2.82 (m, 1H), 2.61 (m, 2H), 2.41 (m, 2H), 1.96 (m, 2H), 1.77-1.5 (m, 6H).

STEP 2 (Synthesis of 3-cyclopentyl-2-iodo-2-cyclopenten-1-one): To a stirred solution of 4.35 g 3-cyclopentyl-2-cyclopenten-1-one in 50 ml carbon tetrachloride, were added 15 g iodine and 2.4 ml pyridine, and the reaction mixture was stirred overnight. The reaction mixture was first diluted with diethyl ether, washed in series with saturated aqueous sodium thiosulfate, aqueous sodium bicarbonate, and brine. The organic layer was dried over anhydrous magnesium sulfate and filtered. The filtrate was concentrated under reduced pressure and purified by column chromatography (silica gel, hexane/ethyl acetate=6:1) to yield 4 g of 3-cyclopentyl-2-iodo-2-cyclopenten-1-one as an oil. $^1$H NMR (CDCl$_3$, 300 MHz): δ 3.23 (m, 1H), 2.74 (m, 2H), 2.57 (m, 2H), 1.98 (m, 2H), 1.78 (m, 4H), 1.55 (m, 2H).

STEP 3 (Synthesis of 3-cyclopentyl-2-(4-fluorophenyl)-2-cyclopenten-1-one): A mixture of 65 mg 3-cyclopentyl-2-iodo-2-cyclopenten-1-one, 40 mg 4-fluorophenylboronic acid, 10 mg tetrakis(triphenylphosphine)palladium, 4 ml toluene, 2 ml ethanol and 1.5 ml 2N aqueous sodium carbonate was subjected to Suzuki coupling by stirring at 80° C. overnight. The reaction mixture was diluted with ethyl acetate, washed with brine, dried over anhydrous magnesium sulfate, and filtered. The filtrate was concentrated under reduced pressure and purified by column chromatography (silica gel, hexane/ethyl acetate=4:1) to yield 52 mg of 3-cyclopentyl-2-(4-fluorophenyl)-2-cyclopenten-1-one as a solid. $^1$H NMR (CDCl$_3$, 300 MHz): δ 7.22 (m, 2H), 7.09 (m, 2H), 3.15 (m, 1H), 2.68 (m, 2H), 2.55 (m, 2H), 1.81 (m, 4H), 1.64 (m, 4H).

STEP 4 (Synthesis of 3-cyclopentyl-2-(4-fluorophenyl)-2-cyclopenten-1-one oxime): A mixture of 50 mg 3-cyclopentyl-2-(4-fluorophenyl)-2-cyclopenten-1-one and 20 mg hydroxylamine hydrochloride in 5 ml pyridine was stirred at 60° C. overnight. Pyridine was removed under reduced pressure, and the resulting residue was subjected to extraction with ethyl acetate and 10% aqueous HCl. The organic layer was washed with aqueous sodium bicarbonate and brine, dried over anhydrous magnesium sulfate, and filtered. Then the filtrate was concentrated under reduced pressure and purified by column chromatography (silica gel, hexane/ethyl acetate=4:1) to yield 40 mg of 3-cyclopentyl-2-(4-fluorophenyl)-2-cyclopenten-1-one oxime as a solid. mp=204-205° C.; $^1$H NMR (CDCl$_3$, 300 MHz): δ 7.24-7.19 (m, 2H), 7.11-7.04 (m, 2H), 6.73 (bs, 1H), 2.89 (m, 1H), 2.80 (m, 2H), 2.61 (m, 2H), 1.70 (m, 4H), 1.55 (m, 4H); APCI MS: m/z 260.1 (M+1).

EXAMPLES 2~22

The compounds listed in Table 2 below were prepared according to a procedure similar to that employed for Example 1. The following aryl or heteroaryl boronic acids were adopted for the Suzuki coupling reaction in STEP 3 in the preparation of Examples 2~22: 3,4-difluorophenylboronic acid for Example 2; 3-chloro-4-fluorophenylboronic acid for Example 3; 3-nitrophenylboronic acid for Example 4; 4-methyl-3-nitrophenylboronic acid for Example 5; 3,4-dimethoxyphenylboronic acid for Example 6; 3-methoxyphenylboronic acid for Example 7; 4-methoxy-3-methoxymethylphenylboronic acid for Example 8; 4-benzyloxyphenylboronic acid for Example 9; 3,4-methylenedioxyphenylboronic acid for Example 10; 3-trifluoromethoxyphenylboronic acid for Example 11; 3-cyanophenylboronic acid for Example 12; 3-cyano-4-fluorophenylboronic acid for Example 13; N,N-dimethylaminomethylphenyl-3-boronic acid pinacol ester for Example 14; 3-dimethylaminophenylboronic acid for Example 15; 5-indolylboronic acid for Example 16; 6-methoxy-2-naphthaleneboronic acid for Example 17; 4-vinylbenzeneboronic acid for Example 18; dibenzofuran-4-boronic acid for Example 19; thianthrene-1-boronic acid for Example 20; benzamide-3-boronic acid for Example 21; and 3-methylthiophenylboronic acid for Example 22. Spectral data for Examples 2~22 are provided along with their melting points in Table 2.

TABLE 2

Physical characterization data for Examples 2~22.

| Example | R$_2$ | Spectral Data | mp, ° C. |
|---|---|---|---|
| 2 | 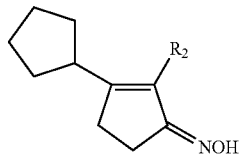 | $^1$H NMR (CDCl$_3$, 300 MHz): δ 7.36 (bs, 1H), 7.16 (dt, J=10.5 and 8.4 Hz, 1H), 7.07 (ddd, J=2.1, 7.8 and 11.1 Hz, 1H), 6.96 (m, 1H), 2.88 (m, 1H), 2.77 (m, 2H), 2.61 (m, 2H), 1.70 (m, 4H), 1.55 (m, 4H); APCI MS: m/z 278.1 (M + 1) | 173-174 |

TABLE 2-continued

Physical characterization data for Examples 2~22.

[Structure: cyclopentyl-substituted cyclopentenone oxime with R2 group]

| Example | R$_2$ | Spectral Data | mp, ° C. |
|---|---|---|---|
| 3 | 4-F, 3-Cl phenyl | $^1$H NMR (CDCl$_3$, 300 MHz): δ 7.29 (dd, J=1.8 and 7.2 Hz, 1H), 7.15-7.07 (m, 3H), 2.86 (m, 1H), 2.79 (m, 2H), 2.60 (m, 2H), 1.70 (m, 4H), 1.55 (m, 4H) | 143-144 |
| 4 | 3-NO$_2$ phenyl | $^1$H NMR (CDCl$_3$, 300 MHz): δ 8.17 (m, 2H), 7.58 (m, 2H), 6.78 (s, 1H), 2.84 (m, 3H), 2.66 (m, 2H), 1.74 (m, 4H), 1.56 (m, 4H); APCI MS: m/z 287.1 (M + 1) | 162-163 |
| 5 | 2-Me, 3-NO$_2$ phenyl | $^1$H NMR (CDCl$_3$, 300 MHz): δ 8.01 (bs, 1H), 7.88 (d, J=1.5 Hz, 1H), 7.39 (dd, J=1.5 and 7.8 Hz, 1H), 7.34 (d, J=7.8 Hz, 1H), 2.87 (m, 1H), 2.77 (m, 2H), 2.63 (m, 2H), 2.60 (s, 3H), 1.70 (m, 4H), 1.55 (m, 4H) | 178-180 |
| 6 | 3,4-diOMe phenyl | $^1$H NMR (CDCl$_3$, 300 MHz): δ 7.48 (bs, 1H), 6.89 (m, 1H), 6.80 (m, 2H), 3.89 (s, 3H), 3.87 (s, 3H), 2.96 (m, 1H), 2.78 (m, 2H), 2.58 (m, 2H), 1.71 (m, 4H), 1.56 (m, 4H) | 154-155 |
| 7 | 3-OMe phenyl | $^1$H NMR (CDCl$_3$, 300 MHz): δ 7.34 (bs, 1H), 7.29 (t, J=8.1 Hz, 1H), 6.86-6.78 (m, 3H), 3.81 (s, 3H), 2.94 (m, 1H), 2.78 (m, 2H), 2.59 (m, 2H), 1.70 (m, 4H), 1.56 (m, 4H) | 132-133 |
| 8 | 4-OMe, 2-CH$_2$OMe phenyl | $^1$H NMR (CDCl$_3$, 300 MHz): δ 7.25 (d, J=2.1 Hz, 1H), 7.16 (dd, J=8.7 Hz, 1H), 6.89 (d, J=8.7 Hz, 1H), 6.63 (bs, 1H), 4.51 (s, 2H), 3.84 (s, 3H), 3.41 (s, 3H), 2.94 (m, 1H), 2.79 (m, 2H), 2.59 (m, 2H), 1.70 (m, 4H), 1.55 (m, 4H) | 134-135 |
| 9 | 4-OBn phenyl | $^1$H NMR (CDCl$_3$, 300 MHz): δ 7.43-7.39 (m, 5H), 7.19 (d, J=8.1 Hz, 2H), 7.00 (d, J=8.1 Hz, 2H), 5.07 (s, 2H), 2.92 (m, 1H), 2.79 (m, 2H), 2.59 (m, 2H), 1.70-1.55 (m, 8H) | 189-190 |
| 10 | 3,4-methylenedioxyphenyl | $^1$H NMR (CDCl$_3$, 300 MHz): δ 6.83 (d, J=7.8 Hz, 1H), 6.56 (m, 2H), 5.96 (s, 2H), 2.92 (m, 1H), 2.60 (m, 2H), 2.77 (m, 2H), 1.70 (m, 4H), 1.54 (m, 4H) | 186-188 |
| 11 | 3-OCF$_3$ phenyl | $^1$H NMR (CDCl$_3$, 300 MHz): δ 7.43-7.38 (m, 2H), 7.21-7.11 (m, 3H), 2.94-2.84 (m, 1H), 2.81-2.77 (m, 2H), 2.63-2.60 (m, 2H), 1.77-1.62 (m, 4H), 1.60-1.50 (m, 4H) | 145-146 |
| 12 | 3-CN phenyl | $^1$H NMR (CDCl$_3$, 300 MHz): δ 7.79 (bs, 1H), 7.59 (m, 1H), 7.54 (s, 1H), 7.49 (m, 2H), 2.79 (m, 3H), 2.63 (m, 2H), 1.72 (m, 4H), 1.56 (m, 4H) | 180-182 |
| 13 | 2-F, 3-CN phenyl | $^1$H NMR (CDCl$_3$, 300 MHz): δ 8.23 (s, 1H), 7.47 (m, 2H), 7.22 (t, J=8.7 Hz, 1H), 2.82-2.74 (m, 3H), 2.65-2.60 (m, 2H), 1.80-1.65 (m, 4H), 1.64-1.52 (m, 4H) | 167-168 |

TABLE 2-continued

Physical characterization data for Examples 2~22.

| Example | R₂ | Spectral Data | mp, ° C. |
|---|---|---|---|
| 14 | 3-(dimethylaminomethyl)phenyl (—C₆H₄—CH₂—NMe₂) | ¹H NMR (CDCl₃, 300 MHz): δ 7.58 (dd, J=7.5 and 8.1 Hz, 1H), 7.53 (dt, J=8.1 and 1.6 Hz, 1H), 7.45 (t, J=1.6 Hz, 1H), 7.42 (dt, J=7.5 and 1.6 Hz, 1H), 2.97 (m, 1H), 2.95 (s, 6H), 2.87 (m, 2H), 2.73 (m, 2H), 1.83-1.78 (m, 4H), 1.67-1.64 (m, 4H) | 280 (dec.) |
| 15 | 3-(dimethylamino)phenyl | ¹H NMR (CDCl₃, 300 MHz): δ 7.62 (bs, 1H), 7.24 (t, J=8.1 Hz, 1H), 6.68 (ddd, J=1.0, 2.6 and 8.1 Hz, 1H), 6.60 (m, 2H), 3.01 (m, 1H), 2.94 (s, 6H), 2.81-2.77 (m, 2H), 2.61-2.57 (m, 2H), 1.77-1.62 (m, 4H), 1.60-1.50 (m, 4H) | 136-143 |
| 16 | 1H-indol-5-yl | ¹H NMR (CDCl₃, 300 MHz): δ 9.51 (bs, 1H), 8.87 (bs, 1H), 8.48 (s, 1H), 7.38-7.30 (m, 1H), 7.18 (t, J=2.7 Hz, 1H), 7.05 (d, J=8.4 Hz, 1H), 6.45 (m, 1H), 3.03-2.98 (m, 1H), 2.81-2.77 (m, 2H), 2.61-2.57 (m, 2H), 1.77-1.62 (m, 4H), 1.60-1.50 (m, 4H) | 230 (dec.) |
| 17 | 6-methoxy-2-naphthyl | ¹H NMR (CDCl₃, 300 MHz): δ 7.74 (m, 2H), 7.63 (s, 1H), 7.35 (m, 1H), 7.14 (m, 2H), 3.93 (s, 3H), 2.98 (m, 1H), 2.82 (m, 2H), 2.65 (m, 2H), 1.70 (m, 4H), 1.54 (m, 4H) | 185-186 |
| 18 | 4-vinylphenyl | 7.43 (m, 2H), 7.36 (bs, 1H), 7.22 (m, 2H), 6.74 (m, 1H), 5.76 (dd, J=11.1 and 1.2 Hz, 1H), 5.25 (dd, J=17.1 and 0.9 Hz, 1H), 2.98 (m, 1H), 2.80 (m, 2H), 2.61 (m, 2H), 1.74-1.69 (m, 4H), 1.59-1.53 (m, 4H) | 177-179 |
| 19 | dibenzofuran-4-yl | ¹H NMR (CDCl₃, 300 MHz): δ 7.96 (d, J=7.5 Hz, 1H), 7.92 (dd, J=1.6 and 7.1 Hz, 1H), 7.54 (d, J=8.1 Hz, 1H), 7.46-7.31 (m, 4H), 7.10 (bs, 1H), 2.94-2.84 (m, 2H), 2.81-2.72 (m, 3H), 1.77-1.62 (m, 4H), 1.60-1.50 (m, 4H) | 195-200 |
| 20 | thianthren-1-yl | ¹H NMR (CDCl₃, 300 MHz): δ 7.46 (m, 2H), 7.41 (m, 1H), 7.26 (m, 2H), 7.20 (m, 2H), 7.06 (dd, J=1.5 and 7.5 Hz, 1H), 2.89 (m, 2H), 2.74 (m, 1H), 2.65 (m, 2H), 1.80-1.60 (m, 4H), 1.60-1.40 (m, 4H) | 81-84 |
| 21 | 3-carbamoylphenyl (—C₆H₄—CONH₂) | ¹H NMR (CDCl₃, 300 MHz): δ 10.02 (bs, 1H), 7.81-7.78 (m, 2H), 7.65 (s, 1H), 7.52 (bs, 1H), 7.44-7.34 (m, 2H), 6.51 (bs, 1H), 2.82-2.74 (m, 3H), 2.65-2.60 (m, 2H), 1.80-1.65 (m, 4H), 1.64-1.52 (m, 4H) | 200-206 |
| 22 | 3-(methylthio)phenyl | ¹H NMR (CDCl₃, 300 MHz): δ 7.28 (m, 1H), 7.20 (m, 1H), 7.12 (m, 1H), 7.02 (m, 1H), 6.86 (bs, 1H), 2.91 (m, 1H), 2.80 (m, 2H), 2.61 (m, 2H), 2.48 (s, 3H), 1.71 (m, 4H), 1.56 (m, 4H) | 113-114 |

EXAMPLE 23

3-cyclopentyl-2-(3-methylsulfonylphenyl)-2-cyclopenten-1-one oxime

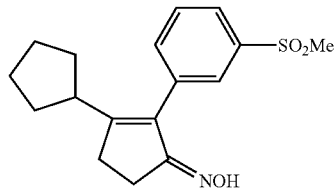

To a solution of 120 mg 3-cyclopentyl-2-(3-methylthiophenyl)-2-cyclopenten-1-one in 12 ml 1:1:1 mixture of THF/methanol/water, was added 800 mg OXONE®, and the reaction mixture was stirred for 3 hours. Then the reaction mixture was concentrated under reduced pressure and extracted with water/ethyl acetate. The organic layer was washed with brine, dried over anhydrous magnesium sulfate, and filtered. The filtrate was concentrated under reduced pressure and purified by column chromatography (silica gel, hexane/ethyl acetate=3:1) to yield 120 mg 3-cyclopentyl-2-(3-methylsulfonylphenyl)-2-cyclopenten-1-one. The methylsulfone compound was condensed with hydroxylamine hydrochloride according to a procedure similar to that described in STEP 4 for Example 1 to afford 80 mg of 3-cyclopentyl-2-(3-methylsulfonylphenyl)-2-cyclopenten-1-one oxime as a solid. mp=164-165° C.; $^1$H NMR (CDCl$_3$, 300 MHz): δ 7.90-7.85 (m, 2H), 7.62-7.52 (m, 2H), 7.19 (bs, 1H), 3.08 (s, 3H), 2.85 (m, 1H), 2.80 (m, 2H), 2.64 (m, 2H), 1.73 (m, 4H), 1.58 (m, 4H); APCI MS: m/z 320.1 (M+1).

EXAMPLE 24

3-cyclopentyl-2-(3-hydroxyphenyl)-2-cyclopenten-1-one oxime

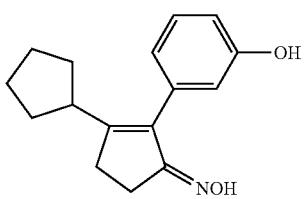

To a stirred solution of 27 mg 3-cyclopentyl-2-(3-methoxyphenyl)-2-cyclopenten-1-one oxime (Example 7) in 5 ml dichloromethane at −78° C., was added 0.5 ml 1.0 M boron tribromide in hexane dropwise under inert atmosphere. The reaction mixture was stirred for 2 hours while being allowed to gradually warm to room temperature. Then the reaction mixture was poured into saturated aqueous sodium carbonate, and extracted with ethyl acetate. The organic layer was washed with brine, dried over anhydrous magnesium sulfate, and filtered. The filtrate was concentrated under reduced pressure and purified by column chromatography (silica gel, hexane/ethyl acetate=1:1) to yield 12 mg of 3-cyclopentyl-2-(3-hydroxyphenyl)-2-cyclopenten-1-one oxime. mp=207-209° C.; $^1$H NMR (CDCl$_3$, 300 MHz): δ 7.26-7.21 (m, 2H), 6.79-6.70 (m, 3H), 2.93 (m, 1H), 2.80 (m, 2H), 2.61 (m, 2H), 1.70 (m, 4H), 1.54 (m, 4H); APCI MS: m/z 258.1 (M+1).

EXAMPLE 25

3-cyclopentyl-2-(3-hydroxymethylphenyl)-2-cyclopenten-1-one oxime

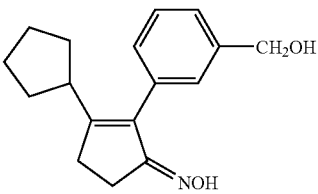

A mixture of 120 mg 3-cyclopentyl-2-iodo-2-cyclopenten-1-one, 80 mg 3-formylphenylboronic acid and 20 mg tetrakis (triphenylphosphine)palladium was stirred at 80° C. overnight in 8 ml toluene, 4 ml ethanol and 4 ml 2 N aqueous sodium carbonate. Then the reaction mixture was diluted with ethyl acetate, washed with brine, dried over anhydrous magnesium sulfate, and filtered. The filtrate was concentrated under reduced pressure and purified by column chromatography (silica gel, hexane/ethyl acetate=2:1) to yield 70 mg of 3-cyclopentyl-2-(3-formylphenyl)-2-cyclopenten-1-one. 3-cyclopentyl-2-(3-formylphenyl)-2-cyclopenten-1-one in benzene was stirred with one drop of acetic acid and 100 mg sodium triacetoxyborohydride at 70-80° C. for 2 hours. Then the reaction mixture was poured into saturated aqueous ammonium chloride, and extracted with ethyl acetate. The organic layer was washed with brine, dried over anhydrous magnesium sulfate, and filtered. The filtrate was concentrated under reduced pressure and purified by column chromatography (silica gel, hexane/ethyl acetate=2:1) to yield 40 mg of 3-cyclopentyl-2-(3-hydroxymethylphenyl)-2-cyclopenten-1-one, which was then condensed with hydroxylamine hydrochloride according to a procedure similar to that described in STEP 4 for Example 1 to afford 20 mg of 3-cyclopentyl-2-(3-hydroxymethylphenyl)-2-cyclopenten-1-one oxime as a solid. $^1$H NMR (CDCl$_3$, 300 MHz): δ 8.75 (bs, 1H), 7.40-7.29 (m, 3H), 7.12 (d, J=7.2 Hz, 1H), 4.66 (s, 2H), 2.98 (m, 1H), 2.75 (m, 2H), 2.61 (m, 2H), 1.71 (m, 4H), 1.55 (m, 4H).

EXAMPLE 26

3-cyclopentyl-2-(4-hydroxymethylphenyl)-2-cyclopenten-1-one oxime

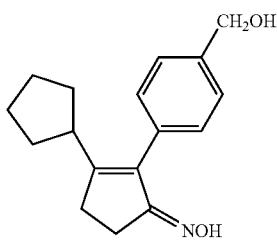

The titled compound was prepared according to a procedure similar to that employed for Example 25. It is noted that 4-formylphenyl boronic acid was used for Example 26 in place of 3-formylphenyl boronic acid used for Example 25. mp=187-190° C.; $^1$H NMR (CDCl$_3$, 300 MHz): δ 7.39 (d, J=7.5 Hz, 2H), 7.25 (d, J=7.5 Hz, 2H), 6.79 (bs, 1H), 4.70 (s, 2H), 2.91 (m, 1H), 2.80 (m, 2H), 2.61 (m, 2H), 1.70 (m, 4H), 1.55 (m, 4H); APCI MS: m/z 272.2 (M+1).

EXAMPLE 27

3-cyclohexyl-2-(4-fluorophenyl)-2-cyclopenten-1-one oxime

The titled compound was prepared according to the four step procedure as provided below.

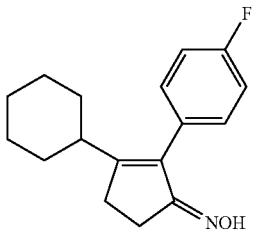

STEP 1 (Synthesis of 3-cyclohexyl-2-cyclopenten-1-one): To a stirred solution of 45 ml 2.0 M cyclohexyl magnesium chloride in diethyl ether and 15 ml diethyl ether at 0° C., was added dropwise 4.8 g 2-cyclopenten-1-one dissolved in 10 ml diethyl ether under inert atmosphere. The reaction mixture was stirred for an hour while being allowed to warm to room temperature, poured into saturated aqueous ammonium chloride, and extracted with ethyl acetate. The organic layer was washed with brine, dried over anhydrous magnesium sulfate, and filtered. The filtrate was concentrated under reduced pressure, and then the resulting residue was reacted with 15 g pyridinium chlorochromate (PCC) in the presence of an appropriate amount of celite in 100 ml methylenechloride for 4 hours. The reaction mixture was diluted with 100 ml diethyl ether and filtered through a silica-gel pad. The filtrate was concentrated under reduced pressure and purified by column chromatography (silica gel, hexane/ethyl acetate=5:1) to yield 1.5 g of 3-cyclohexyl-2-cyclopenten-1-one as an oil. $^1$H NMR (CDCl$_3$, 300 MHz): δ 5.93 (m, 1H), 2.61 (m, 2H), 2.39 (m, 2H), 2.30 (m, 1H), 1.91-1.19 (m, 10H).

STEP 2 (Synthesis of 3-cyclohexyl-2-iodo-2-cyclopenten-1-one): To a stirred solution of 1.05 g 3-cyclohexyl-2-cyclopenten-1-one in 20 ml carbon tetrachloride, were added 5 g iodine and 0.6 ml pyridine in series, and the mixture was stirred overnight. The reaction mixture was diluted with diethyl ether, washed in sequence with saturated aqueous sodium thiosulfate, aqueous sodium bicarbonate, and brine. The organic layer was dried over anhydrous magnesium sulfate and filtered. Then the filtrate was concentrated under reduced pressure and purified by column chromatography (silica gel, hexane/ethyl acetate=6:1) to yield 850 mg of 3-cyclohexyl-2-iodo-2-cyclopenten-1-one as an oil. $^1$H NMR (CDCl$_3$, 300 MHz): δ 2.81 (m, 1H), 2.72 (m, 2H), 2.55 (m, 2H), 1.90-1.20 (m, 10H).

STEP 3 (Synthesis of 3-cyclohexyl-2-(4-fluorophenyl)-2-cyclopenten-1-one): 160 mg 3-cyclohexyl-2-iodo-2-cyclopenten-1-one, 100 mg 4-fluorophenylboronic acid, and 25 mg tetrakis(triphenylphosphine)palladium were stirred at 80° C. overnight in 5 ml toluene, 2.5 ml ethanol, and 2 ml 2 N aqueous sodium carbonate. The reaction mixture was diluted with ethyl acetate, washed with brine, dried over anhydrous magnesium sulfate, and filtered. Then the filtrate was concentrated under reduced pressure and was purified by column chromatography (silica gel, hexane/ethyl acetate=4:1) to yield 120 mg of 3-cyclohexyl-2-(4-fluorophenyl)-2-cyclopenten-1-one as an oil. $^1$H NMR (CDCl$_3$, 300 MHz): δ 7.18 (m, 2H), 7.10 (m, 2H), 2.76 (m, 1H), 2.66 (m, 2H), 2.52 (m, 2H), 1.82-1.20 (m, 10H).

STEP 4 (Synthesis of 3-cyclohexyl-2-(4-fluorophenyl)-2-cyclopenten-1-one oxime): A mixture of 120 mg 3-cyclohexyl-2-(4-fluorophenyl)-2-cyclopenten-1-one and 60 mg hydroxylamine hydrochloride was stirred in 10 ml pyridine at 60° C. overnight. Pyridine was removed under reduced pressure, and the resulting residue was dissolved in ethyl acetate and washed with 10% aqueous HCl. The organic layer was washed with aqueous sodium bicarbonate and brine, dried over anhydrous magnesium sulfate, and filtered. Then the filtrate was concentrated under reduced pressure and purified by recrystallization (ethyl acetate-hexane) to yield 40 mg of 3-cyclohexyl-2-(4-fluorophenyl)-2-cyclopenten-1-one oxime as a solid. mp=173-176 ° C.; $^1$H NMR (CDCl$_3$, 300 MHz): δ 7.20 (m, 2H), 7.08 (m, 2H), 6.78 (bs, 1H), 2.77 (m, 2H), 2.59 (m, 2H), 2.47 (m, 1H), 1.75-1.16 (m, 10H); APCI MS: m/z 274.2 (M+1).

EXAMPLES 28~32

The compounds listed in Table 3 below were prepared according to a procedure similar to that employed for Example 27. The following phenylboronic acids were adopted for the Suzuki coupling reaction in STEP 3 in the preparation of Examples 28~32: 3-chloro-4-fluorophenylboronic acid for Example 28; 3-fluorophenylboronic acid for Example 29; 3,4-difluorophenylboronic acid for Example 30; 3-nitrophenylboronic acid for Example 31; and 3-methoxyphenylboronic acid for Example 32. Spectral data for Examples 28-32 are provided along with their melting points in Table 3.

TABLE 3

Physical characterization data for Examples 28~32.

| Example | R$_2$ | Spectral Data | mp, ° C. |
|---|---|---|---|
| 28 | 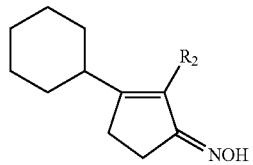 | $^1$H NMR (CDCl$_3$, 300 MHz): δ 7.28 (dd, J=2.1 and 6.9 Hz, 1H), 7.16 (t, J=8.7 Hz, 1H), 7.08 (ddd, J=2.1, 4.8 and 8.7 Hz, 1H), 6.93 (bs, 1H), 2.77 (m, 2H), 2.59 (m, 2H), 2.45 (m, 1H), 1.75-1.16 (m, 10H) | 158-160 |

TABLE 3-continued

Physical characterization data for Examples 28~32.

| Example | R₂ | Spectral Data | mp, ° C. |
|---|---|---|---|
| 29 | 3-fluorophenyl | ¹H NMR (CDCl₃, 300 MHz): δ 7.28 (dd, J=2.1 and 6.9 Hz, 1H), 7.16 (t, J=8.7 Hz, 1H), 7.08 (ddd, J=2.1, 4.8 and 8.7 Hz, 1H), 6.93 (bs, 1H), 2.77 (m, 2H), 2.59 (m, 2H), 2.45 (m, 1H), 1.75-1.16 (m, 10H) | 199-201 |
| 30 | 3,4-difluorophenyl | ¹H NMR (CDCl₃, 300 MHz): δ 7.19 (dt, J=10.2 and 8.4 Hz, 1H), 7.06 (ddd, J=2.1, 7.5 and 11.1 Hz, 1H), 6.94 (m, 2H), 2.77 (m, 2H), 2.58 (m, 2H), 2.46 (m, 1H), 1.76-1.16 (m, 10H) | |
| 31 | 3-nitrophenyl | ¹H NMR (CDCl₃, 300 MHz): δ 8.18 (m, 1H), 8.13 (m, 1H), 7.56 (m, 2H), 7.06 (bs, 1H), 2.79 (m, 2H), 2.65 (m, 2H), 2.44 (m, 1H), 1.75-1.16 (m, 10H) | 201-202 |
| 32 | 3-methoxyphenyl | ¹H NMR (CDCl₃, 300 MHz): δ 7.30 (t, J=7.8 Hz, 1H), 6.88-6.76 (m, 4H), 3.81 (s, 3H), 2.78 (m, 2H), 2.58 (m, 2H), 2.53 (m, 1H), 1.74-1.16 (m, 10H) | 149-150 |

EXAMPLE 33

3-butyl-2-(4-fluorophenyl)-2-cyclopenten-1-one oxime

The titled compound was prepared according to the four step procedure as provided below.

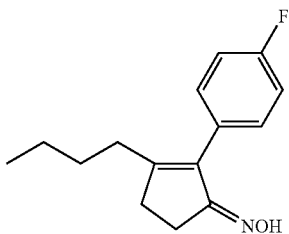

STEP 1 (Synthesis of 3-butyl-2-cyclopenten-1-one): To a stirred solution of 690 mg 3-ethoxy-2-cyclopenten-1-one in 10 ml THF, was added dropwise 3 ml 2.5 M solution of n-butyllithium in hexane at 0° C. under inert atmosphere. The reaction mixture was allowed to warm to room temperature and stirred for another 2 hours. The reaction was quenched by adding 3 N aqueous HCl. The mixture was stirred for another 10 min and subjected to extraction with ethyl acetate. The organic layer was washed with water and brine, dried over anhydrous magnesium sulfate, and filtered. The filtrate was concentrated under reduced pressure and purified by column chromatography (silica gel, hexane/ethyl acetate=5:1) to yield 440 mg of 3-butyl-2-cyclopenten-1-one as an oil. ¹H NMR (CDCl₃, 300 MHz): δ 5.95 (m, 1H), 2.58 (m, 2H), 2.41 (m, 4H), 1.57 (m, 2H), 1.38 (m, 2H), 0.94 (t, J=7.5 Hz, 3H).

STEP 2 (Synthesis of 3-butyl-2-iodo-2-cyclopenten-1-one): To a stirred solution of 400 mg 3-butyl-2-cyclopenten-1-one in 10 ml carbon tetrachloride, were added 1 g iodine and 0.3 ml pyridine. After being stirred overnight, the reaction mixture was diluted with diethyl ether, washed in series with saturated aqueous sodium thiosulfate, aqueous sodium bicarbonate, and brine. The organic layer was dried over anhydrous magnesium sulfate and filtered. Then the filtrate was concentrated under reduced pressure and purified by column chromatography (silica gel, hexane/ethyl acetate=5:1) to yield 500 mg of 3-butyl-2-iodo-2-cyclopenten-1-one as an oil. ¹H NMR (CDCl₃, 300 MHz): δ 2.77 (m, 2H), 2.59 (m, 4H), 1.58 (m, 2H), 1.43 (m, 2H), 0.97 (t, J=7.2 Hz, 3H).

STEP 3 (Synthesis of 3-butyl-2-(4-fluorophenyl)-2-cyclopenten-1-one): 500 mg 3-butyl-2-iodo-2-cyclopenten-1-one, 320 mg 4-fluorophenylboronic acid, and 90 mg tetrakis(triphenylphosphine)palladium were combined and stirred overnight at 80° C. in 20 ml toluene, 10 ml ethanol and 10 ml 2 N aqueous sodium carbonate. The reaction mixture was diluted with ethyl acetate and washed with brine. The organic layer was dried over anhydrous magnesium sulfate and filtered. The filtrate was concentrated under reduced pressure and purified by column chromatography (silica gel, hexane/ethyl acetate=5:1) to yield 420 mg of 3-butyl-2-(4-fluorophenyl)-2-cyclopenten-1-one as an oil. ¹H NMR (CDCl₃, 300 MHz): δ 7.21 (m, 2H), 7.10 (m, 2H), 2.68 (m, 2H), 2.56 (m, 2H), 2.51 (m, 2H), 1.55 (m, 2H), 1.34 (m, 2H), 0.89 (t, J=7.2 Hz, 3H).

STEP 4 (Synthesis of 3-butyl-2-(4-fluorophenyl)-2-cyclopenten-1-one oxime): A mixture of 100 mg 3-butyl-2-(4-fluorophenyl)-2-cyclopenten-1-one and 50 mg hydroxylamine hydrochloride in 10 ml pyridine was stirred at 60° C. overnight. Pyridine was removed under reduced pressure, and the residue was extracted with ethyl acetate and 10% aqueous HCl. The organic layer was washed with aqueous sodium bicarbonate and brine, dried over anhydrous magnesium sulfate, and filtered. Then the filtrate was concentrated under reduced pressure and purified by recrystallization (hexane/ethyl acetate) to yield 80 mg of 3-butyl-2-(4-fluorophenyl)-2-cyclopenten-1-one oxime as a solid. mp=115-116° C.; $^1$H NMR (CDCl$_3$, 300 MHz): δ 7.20 (m, 2H), 7.07 (m, 2H), 2.79 (m, 2H), 2.59 (m, 2H), 2.26 (t, J=7.8 Hz, 2H), 1.45 (m, 2H), 1.26 (m, 2H), 0.85 (t, J=7.4 Hz, 3H); APCI MS: m/z 248.2 (M+1).

EXAMPLES 34~64 EXCLUDING EXAMPLES 41 AND 47~49

These Compounds were prepared according to a procedure similar to that employed for Example 33. The following aryl or heteroaryl boronic acids were adopted for the Suzuki coupling reaction in STEP 3 in the preparation of Examples 34~64: 3,4-difluorophenylboronic acid for Example 34; 2-fluorophenylboronic acid for Example 35; 2,4-difluorophenylboronic acid for Example 36; 3-bromophenylboronic acid for Example 37; 3,4-dichlorophenylboronic acid for Example 38; 3-nitrophenylboronic acid for Example 39; 3-fluoro-4-methoxyphenylboronic acid for Example 40; 3-ethoxyphenylboronic acid for Example 42; 3,4-dimethoxyphenylboronic acid for Example 43; 3-methoxyphenylboronic acid for Example 44; 3,4-methylendioxyphenylboronic acid for Example 45; 4-trifluoromethoxyphenylboronic acid for Example 46; 3-aminophenylboronic acid for Example 50; 3-ethoxycarbonylphenylboronic acid for Example 51; 3-carboxyphenylboronic acid for Example 52; 4-carboxyphenylboronic acid for Example 53; 3,4-dimethylphenylboronic acid for Example 54; 3-methylbenzeneboronic acid for Example 55; 4-butylphenylboronic acid for Example 56; 3-fluoro-4-biphenylboronic acid for Example 57; 3-trifluoromethylphenylboronic acid for Example 58; 4-methansulfinylbenzeneboronic acid for Example 59; 4-methansulfonylbenzeneboronic acid for Example 60; 3-acetamidobenzeneboronic acid for Example 61; 3-acetylbenzeneboronic acid for Example 62; 3-formylbenzeneboronic acid for Example 63; and benzothiophen-2-boronic acid for Example 64. Spectral data for Examples 34~64 are provided along with their melting points in Table 4.

EXAMPLE 41

3-butyl-2-(3-fluoro-4-hydroxyphenyl)-2-cyclopenten-1-one oxime

To a stirred solution of 20 mg 3-butyl-2-(3-fluoro-4-methoxyphenyl)-2-cyclopenten-1-one oxime (Example 40) in 5 ml dichloromethane, was added 0.5 ml 1.0 M boron tribromide in hexane at 0° C. under inert atmosphere. The reaction mixture was stirred for 2 hours, poured into saturated aqueous sodium bicarbonate, and extracted with ethyl acetate. The organic layer was washed with brine, dried over anhydrous magnesium sulfate, and filtered. Then the filtrate was concentrated under reduced pressure and purified by column chromatography (silica gel, hexane/ethyl acetate=2:1) to yield 11 mg 3-butyl-2-(3-fluoro-4-hydroxyphenyl)-2-cyclopenten-1-one oxime. Spectral data for Example 41 are provided along with the melting point in Table 4.

EXAMPLE 47

3-butyl-2-(3-hydroxymethylphenyl)-2-cyclopenten-1-one oxime 3-butyl-2-(3-hydroxymethylphenyl)-2-cyclopenten-1-one oxime was prepared according to a procedure similar to that employed for Example 25. 3-butyl-2-iodo-2-cyclopenten-1-one was used for Example 47 in place of 3-cyclopentyl-2-iodo-2-cyclopenten-1-one for Example 25. Spectral data for Example 47 are provided along with the melting point in Table 4.

EXAMPLE 48

3-butyl-2-(3,4-dihydroxyphenyl)-2-cyclopenten-1-one oxime 3-butyl-2-(3,4-dimethoxyphenyl)-2-cyclopenten-1-one oxime (Example 43) was subjected to demethylation according to a procedure similar to that employed for Example 41 to obtain 3-butyl-2-(3,4-dihydroxyphenyl)-2-cyclopenten-1-one oxime. Spectral data for Example 48 are provided along with the melting point in Table 4.

EXAMPLE 49

3-butyl-2-(3-hydroxyphenyl)-2-cyclopenten-1-one oxime 3-butyl-2-(3-methoxyphenyl)-2-cyclopenten-1-one oxime (Example 44) was subjected to demethylation according to a procedure similar to that employed for Example 41 to obtain 3-butyl-2-(3-hydroxyphenyl)-2-cyclopenten-1-one oxime. Spectral data for Example 49 are provided along with the melting point in Table 4.

TABLE 4

Physical characterization data for Examples 34~64.

| Example | $R_2$ | Spectral Data | mp, ° C. |
|---|---|---|---|
| 34 | 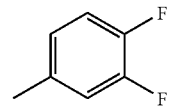 | $^1$H NMR (CDCl$_3$, 300 MHz): δ 8.08 (bs, 1H), 7.16 (m, 1H), 7.06 (m, 1H), 6.95 (m, 1H), 2.77 (m, 2H), 2.58 (m, 2H), 2.27 (t, J=7.8 Hz, 2H), 1.44 (m, 2H), 1.26 (m, 2H), 0.85 (t, J=7.2 Hz, 3H) | |

TABLE 4-continued

Physical characterization data for Examples 34~64.

| Example | R₂ | Spectral Data | mp, ° C. |
|---|---|---|---|
| 35 | 2-F-phenyl | ¹H NMR (CDCl₃, 300 MHz): δ 7.34-7.06 (m, 4H), 2.78 (m, 2H), 2.60 (m, 2H), 2.27 (t, J=7.7 Hz, 2H), 1.45 (m, 2H), 1.27 (m, 2H), 0.86 (t, J=7.4 Hz, 3H). | 105-107 |
| 36 | 2,4-diF-phenyl | ¹H NMR (CDCl₃, 300 MHz): δ 7.02-7.13 (td, J=8.1 and 6.6 Hz, 1H), 7.09 (bs, 1H), 6.94-6.82 (m, 2H), 2.78 (m, 2H), 2.60 (m, 2H), 2.27 (t, J=7.7 Hz, 2H), 1.45 (m, 2H), 1.27 (m, 2H), 0.86 (t, J=7.4 Hz, 3H) | 111-113 |
| 37 | 3-Br-phenyl | ¹H NMR (CDCl₃, 300 MHz): δ 7.63 (bs, 1H), 7.45-7.38 (m, 2H), 7.25 (t, J=7.5 Hz, 1H), 7.18 (dt, J=7.5 and 1.4 Hz, 1H), 2.78 (m, 2H), 2.60 (m, 2H), 2.27 (t, J=7.7 Hz, 2H), 1.45 (m, 2H), 1.27 (m, 2H), 0.86 (t, J=7.4 Hz, 3H) | oil. |
| 38 | 3,4-diCl-phenyl | ¹H NMR (CDCl₃, 300 MHz): δ 8.09 (bs, 1H), 7.44 (d, J=8.1 Hz, 1H), 7.33 (d, J=1.8 Hz, 1H), 7.09 (dd, J=1.8 and 8.1 Hz, 1H), 2.78 (m, 2H), 2.60 (m, 2H), 2.27 (t, J=7.7 Hz, 2H), 1.45 (m, 2H), 1.27 (m, 2H), 0.86 (t, J=7.4 Hz, 3H). | 140-142 |
| 39 | 3-NO₂-phenyl | ¹H NMR (CDCl₃, 300 MHz): δ 8.18-8.11 (m, 2H), 7.91 (bs, 1H), 7.61-7.52 (m, 2H), 2.78 (m, 2H), 2.63 (m, 2H), 2.29 (t, J=7.7 Hz, 2H), 1.48 (m, 2H), 1.27 (m, 2H), 0.85 (t, J=7.1 Hz, 3H) | |
| 40 | 4-OMe-3-F-phenyl | ¹H NMR (CDCl₃, 300 MHz): δ 6.98 (m, 3H), 3.90 (s, 3H), 2.78 (m, 2H), 2.60 (m, 2H), 2.27 (t, J=7.7 Hz, 2H), 1.45 (m, 2H), 1.27 (m, 2H), 0.86 (t, J=7.4 Hz, 3H) | 161-162 |
| 41 | 4-OH-3-F-phenyl | ¹H NMR (CDCl₃, 300 MHz): δ 6.91 (d, J=10.5 Hz, 1H), 6.84 (m, 2H), 2.78 (m, 2H), 2.60 (m, 2H), 2.27 (t, J=7.7 Hz, 2H), 1.45 (m, 2H), 1.27 (m, 2H), 0.86 (t, J=7.4 Hz, 3H); APCI MS: m/z 264.1 (M + 1) | 141-147 |
| 42 | 3-OEt-phenyl | ¹H NMR (CDCl₃, 300 MHz): δ 8.45 (bs, 1H), 6.83 (d, J=7.8 Hz, 1H), 6.43-6.68 (m, 2H), 4.02 (q, J=6.9 Hz, 2H), 2.78 (m, 2H), 2.60 (m, 2H), 2.27 (t, J=7.7 Hz, 2H), 1.45 (m, 2H), 1.39 (t, J=6.9 Hz, 3H), 1.27 (m, 2H), 0.86 (t, J=7.4 Hz, 3H) | 84-85 |
| 43 | 3,4-diOMe-phenyl | ¹H NMR (CDCl₃, 300 MHz): δ 7.02 (bs, 1H), 6.89 (m, 1H), 6.80 (m, 2H), 3.89 (s, 3H), 3.87 (s, 3H), 2.80 (m, 2H), 2.58 (m, 2H), 2.30 (t, J=7.7 Hz, 2H), 1.47 (m, 2H), 1.29 (m, 2H), 0.86 (t, J=7.2 Hz, 3H) | 97-98 |
| 44 | 3-OMe-phenyl | ¹H NMR (CDCl₃, 300 MHz): δ 7.29 (t, J=8.0 Hz, 1H), 7.06 (bs, 1H), 6.86-6.78 (m, 3H), 3.80 (s, 3H), 2.80 (m, 2H), 2.59 (m, 2H), 2.29 (t, J=7.7 Hz, 2H), 1.46 (m, 2H), 1.27 (m, 2H), 0.85 (t, J=7.1 Hz, 3H) | oil |
| 45 | 3,4-methylenedioxy-phenyl | ¹H NMR (CDCl₃, 300 MHz): δ 6.96 (bs, 1H), 6.83 (d, J=7.8 Hz, 1H), 6.43-6.68 (m, 2H), 5.96 (s, 2H), 2.78 (m, 2H), 2.60 (m, 2H), 2.27 (t, J=7.7 Hz, 2H), 1.45 (m, 2H), 1.27 (m, 2H), 0.86 (t, J=7.4 Hz, 3H). | 116-120 |

TABLE 4-continued

Physical characterization data for Examples 34~64.

| Example | R₂ | Spectral Data | mp, °C |
|---|---|---|---|
| 46 | 4-OCF₃-phenyl | ¹H NMR (CDCl₃, 300 MHz): δ 8.32 (bs, 1H), 7.77 (m, 2H), 7.32 (m, 2H), 2.85 (m, 1H), 2.77 (m, 2H), 2.64 (m, 2H), 2.55 (t, J=7.8 Hz, 1H), 2.42 (t, J=8.1 Hz, 1H), 1.54 (m, 2H), 1.40 (m, 2H), 0.92 (m, 3H) | 110-113 |
| 47 | 3-(hydroxymethyl)phenyl | ¹H NMR (CDCl₃, 300 MHz): δ 9.08 (bs, 1H), 7.37 (t, J=7.7 Hz, 1H), 7.34 (m, 1H), 7.29 (m, 1H), 7.12 (m, 1H), 4.65 (s, 2H), 2.74 (m, 2H), 2.62 (bs, 1H), 2.59 (m, 2H), 2.33 (t, J=7.8 Hz, 2H), 1.46 (m, 2H), 1.28 (m, 2H), 0.85 (t, J=7.0 Hz, 3H) | wax |
| 48 | 3,4-dihydroxyphenyl | ¹H NMR (DMSO-d₆) δ 10.20 (bs, 1H), 8.82 (bs, 2H), 6.67 (m, 2H), 6.48 (dd, J=8.0 and 2.0 Hz, 1H), 2.57 (m, 2H), 2.48 (m, 2H), 2.24 (t, J=7.8 Hz, 2H), 1.42 (m, 2H), 1.24 (m, 2H), 0.82 (t, J=7.4 Hz, 3H) | 147-150 |
| 49 | 3-hydroxyphenyl | ¹H NMR (CDCl₃, 300 MHz): δ 7.21 (m, 1H), 6.75-6.68 (m, 3H), 2.80 (m, 2H), 2.59 (m, 2H), 2.28 (t, J=7.7 Hz, 2H), 1.44 (m, 2H), 1.27 (m, 2H), 0.85 (t, J=7.2 Hz, 3H) | 150-151 |
| 50 | 3-aminophenyl | ¹H NMR (CDCl₃, 300 MHz): δ 7.60 (t, J=7.8 Hz, 1H), 6.64-6.57 (m, 3H), 3.65 (bs, 1H), 2.78 (m, 2H), 2.60 (m, 2H), 2.27 (t, J=7.7 Hz, 2H), 1.45 (m, 2H), 1.27 (m, 2H), 0.86 (t, J=7.4 Hz, 3H) | 157-159 |
| 51 | 3-CO₂Et-phenyl | ¹H NMR (CDCl₃, 300 MHz): δ 7.99 (m, 1H), 7.94 (m, 1H), 7.46 (m, 2H), 6.91 (bs, 1H), 4.37 (q, J=7.2 Hz, 2H), 2.82 (m, 2H), 2.62 (m, 2H), 2.28 (t, J=7.9 Hz, 2H), 1.47 (m, 2H), 1.39 (t, J=7.2 Hz, 3H), 1.29 (m, 2H), 0.85 (t, J=7.1 Hz, 3H) | 70-71 |
| 52 | 3-CO₂H-phenyl | ¹H NMR (DMSO-d₆) δ 10.38 (s, 1H), 7.85 (m, 2H), 7.48 (m, 2H), 2.65 (m, 2H), 2.56 (m, 2H), 2.25 (t, J=7.7 Hz, 2H), 1.45 (m, 2H), 1.24 (m, 2H), 0.80 (t, J=7.2 Hz, 3H). <br>¹³C NMR (DMSO-d₆): δ 167.4, 165.9, 156.4, 134.4, 134.2, 133.9, 130.6, 130.5, 128.3, 128.0, 31.6, 29.6, 29.2, 24.7, 22.1, 13.8. | 190-192 |
| 53 | 4-CO₂H-phenyl | ¹H NMR (CDCl₃, 300 MHz): δ 8.02 (d, J=8.1 Hz, 2H), 7.31 (d, J=8.1 Hz, 2H), 2.78 (m, 2H), 2.60 (m, 2H), 2.27 (t, J=7.7 Hz, 2H), 1.45 (m, 2H), 1.27 (m, 2H), 0.86 (t, J=7.4 Hz, 3H) | 162-166 |
| 54 | 2,4-dimethylphenyl | ¹H NMR (CDCl₃, 300 MHz): δ 7.13 (d, J=7.8 Hz, 1H), 7.01-6.95 (m, 2H), 2.78 (m, 2H), 2.60 (m, 2H), 2.27 (t, J=7.7 Hz, 2H), 2.25 (s, 6H), 1.45 (m, 2H), 1.27 (m, 2H), 0.86 (t, J=7.4 Hz, 3H) | 88-89 |
| 55 | 3-methylphenyl | ¹H NMR (CDCl₃, 300 MHz): δ 7.29-7.24 (m, 1H), 7.12-7.01 (m, 3H), 2.78 (m, 2H), 2.60 (m, 2H), 2.26 (s, 3H), 2.27 (t, J=7.7 Hz, 2H), 1.45 (m, 2H), 1.27 (m, 2H), 0.86 (t, J=7.4 Hz, 3H) | 68-71 |

TABLE 4-continued

Physical characterization data for Examples 34~64.

| Example | R₂ | Spectral Data | mp, ° C. |
|---|---|---|---|
| 56 | (4-butylphenyl, methyl-substituted) | ¹H NMR (CDCl₃, 300 MHz): δ 7.55 (bs, 1H), 7.21-7.13 (m, 4H), 2.79 (m, 2H), 2.64-2.56 (m, 6H), 2.30 (t, J=8.1 Hz, 2H), 1.64 (m, 2H), 1.46-1.27 (m, 6H), 0.96-0.84 (m, 6H) | 81-83 |
| 57 | (2-fluoro-4-methylbiphenyl) | ¹H NMR (CDCl₃, 300 MHz): δ 7.59-7.56 (m, 2H), 7.48-7.36 (m, 3H), 7.13-7.06 (m, 3H), 2.82 (m, 2H), 2.63 (m, 2H), 2.35 (t, J=7.7 Hz, 2H), 1.49 (m, 2H), 1.30 (m, 2H), 0.88 (t, J=7.2 Hz, 3H). | 128-130 |
| 58 | (3-trifluoromethylphenyl, methyl) | ¹H NMR (CDCl₃, 300 MHz): δ 7.60-7.41 (m, 4H), 2.78 (m, 2H), 2.60 (m, 2H), 2.27 (t, J=7.7 Hz, 2H), 1.45 (m, 2H), 1.27 (m, 2H), 0.86 (t, J=7.4 Hz, 3H) | 65-67 |
| 59 | (4-methylsulfinylphenyl, methyl) | ¹H NMR (CDCl₃, 300 MHz): δ 8.25 (bs, 1H), 7.66 (d, J=8.4 Hz, 2H), 7.40 (d, J=8.4 Hz, 2H), 2.78 (m, 2H), 2.73 (s, 3H), 2.60 (m, 2H), 2.27 (t, J=7.7 Hz, 2H), 1.45 (m, 2H), 1.27 (m, 2H), 0.86 (t, J=74 Hz, 3H) | 104-109 |
| 60 | (4-methylsulfonylphenyl, methyl) | ¹H NMR (CDCl₃, 300 MHz): δ 7.95 (d, J=8.4 Hz, 2H), 7.44 (d, J=8.4 Hz, 2H), 3.06 (s, 3H), 2.78 (m, 2H), 2.60 (m, 2H), 2.27 (t, J=7.7 Hz, 2H), 1.45 (m, 2H), 1.27 (m, 2H), 0.86 (t, J=7.4 Hz, 3H) | 122-124 |
| 61 | (3-methylphenyl-NH-C(=NOH)CH₃) | ¹H NMR (CDCl₃, 300 MHz): δ 7.51 (d, J=7.5 Hz, 1H), 7.37-7.26 (m, 2H), 7.95 (d, J=7.8 Hz, 1H), 2.78 (m, 2H), 2.60 (m, 2H), 2.27 (t, J=7.7 Hz, 2H), 2.11 (s, 3H) 1.45 (m, 2H), 1.27 (m, 2H), 0.85 (t, J=7.4 Hz, 3H) | 174-176 |
| 62 | (3-methylphenyl-C(=NOH)CH₃) | ¹H NMR (CDCl₃, 300 MHz): δ 7.57-7.51 (m, 2H), 7.39 (t, J=7.7 Hz, 1H), 7.27-7.2 (m, 1H), 2.78 (m, 2H), 2.60 (m, 2H), 2.27 (t, J=7.7 Hz, 2H), 2.27 (s, 3H) 1.45 (m, 2H), 1.27 (m, 2H), 0.85 (t, J=7.4 Hz, 3H) | 155-156 |
| 63 | (3-methylphenyl-CH=NOH) | ¹H NMR (CDCl₃, 300 MHz): δ 8.10 (s, 1H), 7.50 (m, 1H), 7.43-7.38 (m, 2H), 7.26 (m, 1H), 2.78 (m, 2H), 2.60 (m, 2H), 2.27 (t, J=7.7 Hz, 2H), 1.45 (m, 2H), 1.27 (m, 2H), 0.86 (t, J=7.4 Hz, 3H) | 148-149 |
| 64 | (2-methylbenzothiophene) | ¹H NMR (CDCl₃, 300 MHz): δ 7.63 (bs, 1H), 7.29-7.20 (m, 5H), 2.79 (m, 2H), 2.60 (t, J=3.3 Hz, 2H), 2.28 (t, J=8.1 Hz, 2H), 1.46 (m, 2H), 1.27 (m, 2H), 0.85 (t, J=7.2 Hz, 3H) | 64-66 |

EXAMPLE 65

2-(4-fluorophenyl)-3-pentyl-2-cyclopenten-1-one oxime

The titled compound was prepared according to the four step procedure as described below.

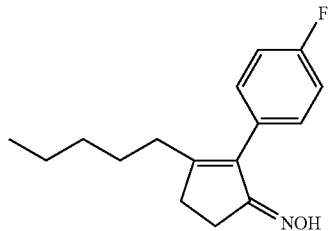

STEP 1 (Synthesis of 3-pentyl-2-cyclopenten-1-one): To a stirred suspension of 2.5 g magnesium in 100 ml diethyl ether, was added 10 ml 1-bromopentane at room temperature under inert atmosphere. One hour later, 5 ml 2-cyclopenten-1-one was added to the mixture slowly. The reaction mixture was stirred for another 2 hours, poured into saturated aqueous ammonium chloride, and extracted with ethyl acetate. The organic layer was washed with brine, dried over anhydrous magnesium sulfate, and filtered. The filtrate was concentrated under reduced pressure, and then the resulting residue was reacted with 10 g PCC in the presence of an appropriate amount of celite in 100 ml dichloromethane for 3 hours. The reaction mixture was diluted with 100 ml diethyl ether and filtered through a silica gel pad. The filtrate was concentrated under reduced pressure and purified by column chromatography (silica gel, hexane/ethyl acetate=10:1) to yield 1.5 g of 3-pentyl-2-cyclopenten-1-one as an oil. $^1$H NMR (CDCl$_3$, 300 MHz): δ 5.92 (m, 1H), 2.57 (m, 2H), 2.39 (m, 4H), 1.57 (m, 2H), 1.32 (m, 4H), 0.88 (m, 3H).

STEP 2 (Synthesis of 2-iodo-3-pentyl-2-cyclopenten-1-one): To a stirred solution of 1.0 g 3-pentyl-2-cyclopenten-1-one in 20 ml carbon tetrachloride, were added in series 1.5 g iodine and 1 ml pyridine. The mixture was stirred overnight, diluted with diethyl ether, washed in series with saturated aqueous sodium thiosulfate, sodium bicarbonate solution and brine, dried over anhydrous magnesium sulfate, and filtered. Then the filtrate was concentrated under reduced pressure and purified by column chromatography (silica gel, hexane/ethyl acetate=7:1) to yield 770 mg of 2-iodo-3-pentyl-2-cyclopenten-1-one as an oil. $^1$H NMR (CDCl$_3$, 300 MHz): δ 2.76 (m, 2H), 2.58 (m, 4H), 1.59 (m, 2H), 1.37 (m, 4H), 0.92 (m, 3H).

STEP 3 (Synthesis of 2-(4-fluorophenyl)-3-pentyl-2-cyclopenten-1-one): A mixture of 2.45 g 2-iodo-3-pentyl-2-cyclopenten-1-one, 1.5 g 4-fluorophenylboronic acid, and 250 mg tetrakis(triphenylphosphine)palladium was stirred at 80° C. overnight in 50 ml toluene, 25 ml ethanol, and 25 ml 2 N aqueous sodium carbonate. The reaction mixture was extracted with ethyl acetate and brine. The organic layer was dried over anhydrous magnesium sulfate and filtered. Then the filtrate was concentrated under reduced pressure and purified by column chromatography (silica gel, hexane/ethyl acetate=5:1) to yield 2.18 g of 2-(4-fluorophenyl)-3-pentyl-2-cyclopenten-1-one. $^1$H NMR (CDCl$_3$, 300 MHz): δ 7.22 (m, 2H), 7.10 (m, 2H), 2.67 (m, 2H), 2.55 (m, 2H), 2.50 (m, 2H), 1.57 (m, 2H), 1.28 (m, 4H), 0.87 (m, 3H).

STEP 4 (Synthesis of 2-(4-fluorophenyl)-3-pentyl-2-cyclopenten-1-one oxime): A mixture of 2.18 g 2-(4-fluorophenyl)-3-pentyl-2-cyclopenten-1-one and 800 mg hydroxylamine hydrochloride in 100 ml pyridine was stirred at 60° C. overnight. Pyridine was removed under reduced pressure, and the resulting residue was extracted with ethyl acetate and 10% aqueous HCl. The organic layer was washed with aqueous sodium bicarbonate solution and brine, dried over anhydrous magnesium sulfate, and filtered. Then the filtrate was concentrated under reduced pressure and purified by recrystallization (ethyl acetate-hexane) to yield 2 g of 2-(4-fluorophenyl)-3-pentyl-2-cyclopenten-1-one oxime. mp=101-102° C.; $^1$H NMR (CDCl$_3$, 300 MHz): δ 9.08 (bs, 1H), 7.19 (m, 2H), 7.04 (m, 2H), 2.72 (m, 2H), 2.54 (m, 2H), 2.24 (t, J=7.8 Hz, 2H), 1.45 (m, 2H), 1.22 (m, 4H), 0.84 (t, J=6.9 Hz, 3H); APCI MS: m/z 262.2 (M+1).

EXAMPLES 66~77

The compounds listed in Table 5 below were prepared according to a procedure similar to that employed for Example 65. The following aryl or heteroaryl boronic acids were adopted for the Suzuki coupling reaction in STEP 3 in the preparation of Examples 66~77: phenylboronic acid for Example 66; 3-fluorophenylboronic acid for Example 67; 3,4-difluorophenylboronic acid for Example 68; 3,5-difluorophenylboronic acid for Example 69; 3-chloro-4-fluorophenylboronic acid for Example 70; 3-nitrophenylboronic acid for Example 71; 3,4,5-trimethoxyphenylboronic acid for Example 72; 4-biphenylboronic acid for Example 73; 4-trifluoromethylphenylboronic acid for Example 74; 2-naphthaleneboronic acid for Example 75; pyridine-3-boronic acid 1,3-propanediol cyclic ester for Example 76; and thiophene-3-boronic acid for Example 77. Spectral data for Examples 66~77 are provided along with their melting points in Table 5.

TABLE 5

Physical characterization data for Examples 66~77.

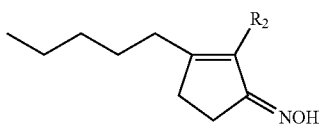

| Example | R$_2$ | Spectral Data | mp, ° C. |
|---|---|---|---|
| 66 | phenyl | $^1$H NMR (CDCl$_3$, 300 MHz): δ 7.41-7.36 (m, 2H), 7.32-7.22 (m, 3H), 6.85 (bs, 1H), 2.81 (m, 2H), 2.60 (m, 2H), 2.28 (t, J=7.8 Hz, 2H), 1.47 (m, 2H), 1.24 (m, 4H), 0.85 (t, J=6.8 Hz, 3H) | 110-111 |

TABLE 5-continued

Physical characterization data for Examples 66~77.

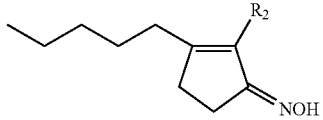

| Example | R₂ | Spectral Data | mp, ° C. |
|---|---|---|---|
| 67 | 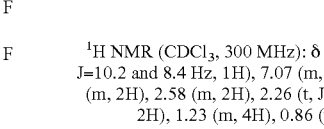 | ¹H NMR (CDCl₃, 300 MHz): δ 7.34 (dt, J=6.0 and 7.8 Hz, 1H), 7.18 (bs, 1H), 7.04-6.94 (m, 3H), 2.80 (m, 2H), 2.60 (m, 2H), 2.27 (t, J=7.8 Hz, 2H), 1.47 (m, 2H), 1.24 (m, 4H), 0.85 (t, J=6.9 Hz, 3H) | 116-117 |
| 68 | 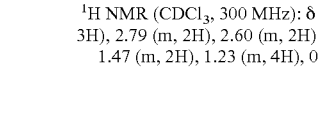 | ¹H NMR (CDCl₃, 300 MHz): δ 8.01 (bs, 1H), 7.16 (dt, J=10.2 and 8.4 Hz, 1H), 7.07 (m, 1H), 6.96 (m, 1H), 2.77 (m, 2H), 2.58 (m, 2H), 2.26 (t, J=7.7 Hz, 2H), 1.46 (m, 2H), 1.23 (m, 4H), 0.86 (t, J=6.8 Hz, 3H) | 69-70 |
| 69 | 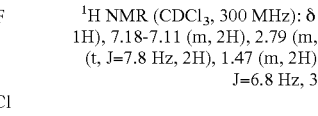 | ¹H NMR (CDCl₃, 300 MHz): δ 7.71 (bs, 1H), 6.77 (m, 3H), 2.79 (m, 2H), 2.60 (m, 2H), 2.28 (t, J=7.8 Hz, 2H), 1.47 (m, 2H), 1.23 (m, 4H), 0.86 (t, J=6.6 Hz, 3H) | 70-71 |
| 70 | 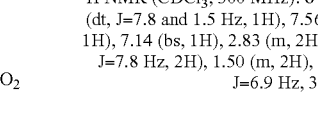 | ¹H NMR (CDCl₃, 300 MHz): δ 7.39 (bs, 1H), 7.30 (m, 1H), 7.18-7.11 (m, 2H), 2.79 (m, 2H), 2.60 (m, 2H), 2.26 (t, J=7.8 Hz, 2H), 1.47 (m, 2H), 1.22 (m, 4H), 0.86 (t, J=6.8 Hz, 3H) | — |
| 71 | 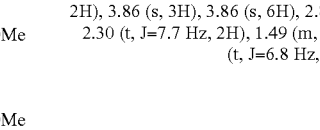 | ¹H NMR (CDCl₃, 300 MHz): δ 8.19-8.14 (m, 2H), 7.61 (dt, J=7.8 and 1.5 Hz, 1H), 7.56 (dt, J=0.6 and 7.5 Hz, 1H), 7.14 (bs, 1H), 2.83 (m, 2H), 2.65 (m, 2H), 2.29 (t, J=7.8 Hz, 2H), 1.50 (m, 2H), 1.24 (m, 4H), 0.86 (t, J=6.9 Hz, 3H). | 79-80 |
| 72 | 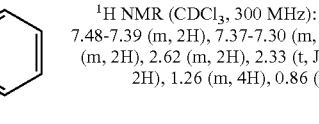 | ¹H NMR (CDCl₃, 300 MHz): δ 7.40 (bs, 1H), 6.46 (s, 2H), 3.86 (s, 3H), 3.86 (s, 6H), 2.80 (m, 2H), 2.59 (m, 2H), 2.30 (t, J=7.7 Hz, 2H), 1.49 (m, 2H), 1.26 (m, 4H), 0.86 (t, J=6.8 Hz, 3H) | 85-86 |
| 73 | 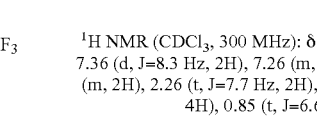 | ¹H NMR (CDCl₃, 300 MHz): δ 7.62-7.59 (m, 4H), 7.48-7.39 (m, 2H), 7.37-7.30 (m, 3H), 7.04 (bs, 1H), 2.83 (m, 2H), 2.62 (m, 2H), 2.33 (t, J=7.8 Hz, 2H), 1.50 (m, 2H), 1.26 (m, 4H), 0.86 (t, J=6.6 Hz, 3H) | 115-116 |
| 74 | 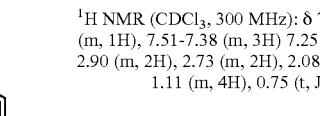 | ¹H NMR (CDCl₃, 300 MHz): δ 7.63 (d, J=8.3 Hz, 2H), 7.36 (d, J=8.3 Hz, 2H), 7.26 (m, 1H), 2.81 (m, 2H), 2.62 (m, 2H), 2.26 (t, J=7.7 Hz, 2H), 1.47 (m, 2H), 1.23 (m, 4H), 0.85 (t, J=6.6 Hz, 3H) | 95-96 |
| 75 | 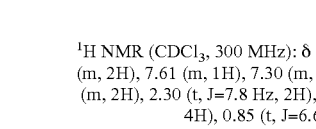 | ¹H NMR (CDCl₃, 300 MHz): δ 7.86-7.80 (m, 2H), 7.67 (m, 1H), 7.51-7.38 (m, 3H) 7.25 (m, 1H), 6.87 (m, 1H), 2.90 (m, 2H), 2.73 (m, 2H), 2.08 (m, 2H), 1.39 (m, 2H), 1.11 (m, 4H), 0.75 (t, J=6.9 Hz, 3H) | 138-139 |
| 76 |  | ¹H NMR (CDCl₃, 300 MHz): δ 8.60 (bs, 1H), 8.68-8.51 (m, 2H), 7.61 (m, 1H), 7.30 (m, 1H), 2.83 (m, 2H), 2.63 (m, 2H), 2.30 (t, J=7.8 Hz, 2H), 1.49 (m, 2H), 1.25 (m, 4H), 0.85 (t, J=6.6 Hz, 3H) | 110-112 |

TABLE 5-continued

Physical characterization data for Examples 66~77.

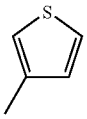

| Example | R₂ | Spectral Data | mp, ° C. |
|---|---|---|---|
| 77 | (3-methylthiophen-2-yl) | ¹H NMR (CDCl₃, 300 MHz): δ 7.60 (bs, 1H), 7.34 (dd, J=3.0 and 4.8 Hz, 1H), 7.26 (dd, J=1.2 and 2.4 Hz, 1H), 7.14 (dd, J=1.2 and 4.8 Hz, 1H), 2.78 (m, 2H), 2.58 (m, 2H), 2.37 (t, J=7.8 Hz, 2H), 1.50 (m, 2H), 1.26 (m, 4H), 0.87 (t, J=6.6 Hz, 3H) | 105-106 |

EXAMPLE 78

2-(4-fluorophenyl)-3-propyl-2-cyclopenten-1-one oxime

The titled compound was prepared according to the four step procedure as provided below.

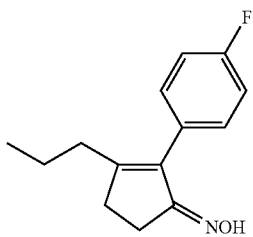

STEP 1 (Synthesis of 3-propyl-2-cyclopenten-1-one): To a stirred solution of 1 ml 2-cyclopenten-1-one in 20 ml diethyl ether at 0° C., was added dropwise 10 ml 2.0 M propyl magnesium chloride in diethyl ether under inert atmosphere. The reaction mixture was stirred for one hour at room temperature, poured into saturated aqueous ammonium chloride, and extracted with ethyl acetate. The organic layer was washed with brine, dried over anhydrous magnesium sulfate, and filtered. The filtrate was concentrated under reduced pressure, and the resulting residue was dissolved in 20 ml dichloromethane and stirred with a mixture of 2.7 g PCC and an appropriate amount of celite for 3 hours. The reaction mixture was diluted with 20 ml diethyl ether and filtered through a silica gel pad. Then the filtrate was concentrated under reduced pressure and purified by column chromatography (silica gel, hexane/ethyl acetate=4:1) to yield 420 mg of 3-propyl-2-cyclopenten-1-one as an oil. ¹H NMR (CDCl₃, 300 MHz): δ 5.95 (m, 1H), 2.58 (m, 2H), 2.41 (m, 4H), 1.63 (m, 2H), 0.98 (t, J=7.2 Hz, 3H).

STEP 2 (Synthesis of 2-iodo-3-propyl-2-cyclopenten-1-one): To a solution of 420 mg 3-propyl-2-cyclopenten-1-one in 10 ml carbon tetrachloride, were added in sequence 2.5 g iodine and 0.4 ml pyridine. After being stirred for 3 hours, the reaction mixture was diluted with diethyl ether, washed in series with saturated aqueous sodium thiosulfate, aqueous sodium bicarbonate, and brine. The organic layer was dried over anhydrous magnesium sulfate and filtered. Then the filtrate was concentrated under reduced pressure and purified by column chromatography (silica gel, hexane/ethyl acetate=4:1) to yield 690 mg of 2-iodo-3-propyl-2-cyclopenten-1-one as an oil. ¹H NMR (CDCl₃, 300 MHz): δ 2.77 (m, 2H), 2.60 (m, 4H), 1.65 (m, 2H), 0.99 (t, J=7.2 Hz, 3H).

STEP 3 (Synthesis of 2-(4-fluorophenyl)-3-propyl-2-cyclopenten-1-one): A mixture of 230 mg 2-iodo-3-propyl-2-cyclopenten-1-one, 160 mg 4-fluorophenylboronic acid, and 40 mg tetrakis(triphenylphosphine)palladium was stirred at 80° C. overnight in 5 ml toluene, 2.5 ml ethanol, and 2.5 ml 2 N aqueous sodium carbonate. The reaction mixture was extracted with ethyl acetate and brine. The organic layer was dried over anhydrous magnesium sulfate and filtered. Then the filtrate was concentrated under reduced pressure and purified by column chromatography (silica gel, hexane/ethyl acetate=5:1) to yield 170 mg of 2-(4-fluorophenyl)-3-propyl-2-cyclopenten-1-one as an oil. ¹H NMR (CDCl₃, 300 MHz): δ 7.21 (m, 2H), 7.10 (m, 2H), 2.67 (m, 2H), 2.55 (m, 2H), 2.50 (m, 2H), 1.61 (m, 2H), 0.94 (t, J=7.2 Hz, 3H).

STEP 4 (Synthesis of 2-(4-fluorophenyl)-3-propyl-2-cyclopenten-1-one oxime): A mixture of 170 mg 2-(4-fluorophenyl)-3-propyl-2-cyclopenten-1-one and 100 mg hydroxylamine hydrochloride was stirred in 20 ml pyridine at 60° C. overnight. Pyridine was removed under reduced pressure, and the resulting residue was extracted with ethyl acetate and 10% aqueous HCl. The organic layer was washed with aqueous sodium bicarbonate and brine, dried over anhydrous magnesium sulfate, and filtered. Then the filtrate was concentrated under reduced pressure and purified by recrystallization (ethyl acetate-hexane) to yield 100 mg of 2-(4-fluorophenyl)-3-propyl-2-cyclopenten-1-one oxime. mp=165-166° C.; ¹H NMR (CDCl₃, 300 MHz): δ 7.24-7.17 (m, 3H), 7.10-7.03 (m, 2H), 2.79 (m, 2H), 2.59 (m, 2H), 2.25 (t, J=7.7 Hz, 2H), 1.50 (m, 2H), 0.87 (t, J=7.4 Hz, 3H); APCI MS: m/z 234.1 (M+1).

EXAMPLE 79

2-(3,4-difluorophenyl)-3-propyl-2-cyclopenten-1-one oxime

The titled compound was prepared according to a procedure similar to that employed for Example 78. 3,4-difluorophenylboronic acid was used for the Suzuki coupling reaction in STEP 3 in the preparation of Example 79. mp=136-137° C.; ¹H NMR (CDCl₃, 300 MHz): δ 7.83 (bs, 1H), 7.17 (dt, J=10.5 and 8.4 Hz, 1H), 7.07 (ddd, J=2.1, 7.8 and 11.1 Hz, 1H), 6.96 (m, 1H), 2.78 (m, 2H), 2.58 (m, 2H), 2.25 (t, J=7.8 Hz, 2H), 1.50 (m, 2H), 0.87 (t, J=7.5 Hz, 3H); APCI MS: m/z 252.1 (M+1).

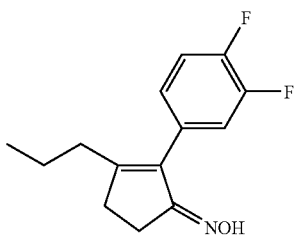

Alternatively, the titled compound was also prepared according to the three step procedure as provided below.

STEP 1 (Synthesis of 1,2-difluoro-4-pent-1-ynylbenzene): To a stirred mixture of 300 mg dichlorobis(triphenylphosphine)palladium and 160 mg copper iodide in 200 ml THF, were added in series 7 ml triethylamine, 10 g 1,2-difluoro-4-iodobenzene, and 4.5 ml pentyne. The reaction mixture was stirred for 8 hours and filtered through a silica gel pad. The filtrate was diluted with ethyl acetate and washed in sequence with 10% aqueous HCl, water, and brine. The organic layer was dried over anhydrous magnesium sulfate and filtered. Then the filtrate was concentrated under reduced pressure and purified by vacuum distillation to yield 7.15 g of 1,2-difluoro-4-pent-1-ynylbenzene as an oil. $^1$H NMR (CDCl$_3$, 300 MHz): δ 7.19 (ddd, J=1.8, 7.8 and 10.8 Hz, 1H), 7.14-7.01 (m, 2H), 2.36 (t, J=7.2 Hz, 2H), 1.62 (qt, J=7.2 and 7.5 Hz, 2H), 1.04 (t, J=7.5 Hz, 3H).

STEP 2 (Synthesis of 2-(3,4-difluorophenyl)-3-propyl-2-cyclopenten-1-one): A steel pressure reactor, charged with 1 g 1,2-difluoro-4-pent-1-ynylbenzene, 385 mg CO$_2$(CO)$_8$, 0.7 ml DMSO, and 35 ml toluene, was purged three times with carbon monoxide, sealed under 5 bar carbon monoxide and 45 bar ethylene, and stirred for 12 hours at 160° C. The reaction mixture was filtered through a celite pad after it was cooled and the pressure was released. Then the filtrate was concentrated under reduced pressure and purified by column chromatography (silica gel, hexane/ethyl acetate=4:1) to yield 1.05 g of 2-(3,4-difluorophenyl)-3-propyl-2-cyclopenten-1-one as an oil. $^1$H NMR (CDCl$_3$, 300 MHz): δ 7.19 (dt, J=10.5 and 8.4 Hz, 1H), 7.09 (ddd, J=2.1, 7.8 and 11.1 Hz, 1H), 6.97 (m, 1H), 2.68 (m, 2H), 2.55 (m, 2H), 2.50 (m, 2H), 1.62 (m, 2H), 0.95 (t, J=7.5 Hz, 3H).

STEP 3 (Synthesis of 2-(3,4-difluorophenyl)-3-propyl-2-cyclopenten-1-one oxime): 1.36 g 2-(3,4-difluorophenyl)-3-propyl-2-cyclopenten-1-one was subjected to condensation with 2.6 g hydroxylamine hydrochloride in 20 ml pyridine to afford 980 mg of 2-(3,4-difluorophenyl)-3-propyl-2-cyclopenten-1-one oxime.

EXAMPLE 80

2-(3-nitrophenyl)-3-propyl-2-cyclopenten-1-one oxime

The titled compound was prepared according to a procedure similar to that employed for Example 78. 3-nitrophenylboronic acid was used for the Suzuki coupling reaction in STEP 3 in the preparation of Example 80. mp=128-129° C.; $^1$H NMR (CDCl$_3$, 300 MHz): δ 8.19-8.14 (m, 2H), 7.63-7.52 (m, 2H), 7.00 (s, 1H), 2.84 (m, 2H), 2.65 (m, 2H), 2.28 (t, J=7.7 Hz, 2H), 1.55 (m, 2H), 0.89 (t, J=7.2 Hz, 3H).

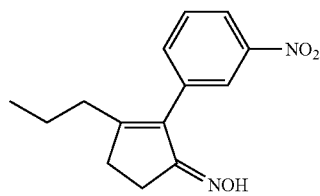

EXAMPLE 81

3-ethyl-2-(4-fluorophenyl)-2-cyclopenten-1-one oxime 3-ethyl-2-cyclopenten-1-one was prepared according to a method similar to the STEP 1 used for Example 78 using ethyl magnesium chloride in place of propyl magnesium chloride. The titled compound was then synthesized starting from 3-ethyl-2-cyclopenten-1-one according to a procedure similar to that employed for Example 78. mp 168-169° C.; $^1$H NMR (CDCl$_3$, 300 MHz): δ 7.24 (m, 2H), 7.08 (m, 2H), 6.89 (s, 1H), 2.81 (m, 2H), 2.61 (m, 2H), 2.30 (q, J=7.8 Hz, 2H), 1.08 (t, J=7.7 Hz, 3H); APCI MS: m/z 220.1 (M+1).

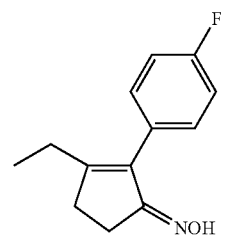

EXAMPLE 82

2-(3,4-difluorophenyl)-3-ethyl-2-cyclopenten-1-one oxime

The titled compound was prepared according to a procedure similar to that employed for Example 81. 3,4-difluorophenylboronic acid was used for the Suzuki coupling in place of 4-fluorophenylboronic acid used for Example 81. mp=136-137° C.; $^1$H NMR (CDCl$_3$, 300 MHz): δ 7.16 (m, 1H), 7.11 (m, 1H), 6.99 (m, 1H), 6.88 (s, 1H), 2.81 (m, 2H), 2.62 (m, 2H), 2.31 (q, J=7.8 Hz, 2H), 1.08 (t, J=7.8 Hz, 3H).

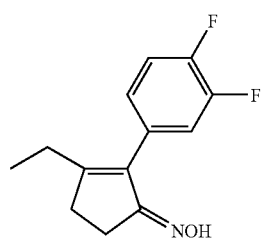

EXAMPLE 83

2-(4-fluorophenyl)-3-methyl-2-cyclopenten-1-one oxime 3-methyl-2-cyclopenten-1-one was prepared according to a method similar to the STEP 1 used for Example 78 using methyl magnesium bromide in place of propyl magnesium chloride. The titled compound was then synthesized starting from 3-methyl-2-cyclopenten-1-one according to a procedure similar to that employed for Example 78. mp 170-171° C.; $^1$H NMR (CDCl$_3$, 300 MHz): δ 7.26 (m, 2H), 7.08 (m, 2H), 6.77 (s, 1H), 2.81 (m, 2H), 2.60 (m, 2H), 1.92 (m, 3H); APCI MS: m/z 206.1 (M+1).

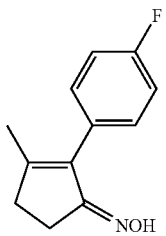

EXAMPLE 84

2-(3,4-difluorophenyl)-3-methyl-2-cyclopenten-1-one oxime

The titled compound was prepared according to a procedure similar to that employed for Example 83. 3,4-difluorophenylboronic acid was used for the Suzuki coupling in place of 4-fluorophenylboronic acid used for Example 83. mp=155-156° C.; $^1$H NMR (CDCl$_3$, 300 MHz): δ 7.19-7.10 (m, 2H), 7.04 (m, 1H), 6.75 (s, 1H), 2.81 (m, 2H), 2.60 (m, 2H), 1.94 (m, 3H).

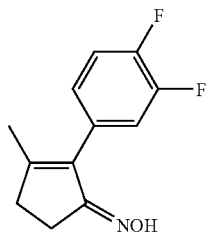

EXAMPLE 85

2-(4-fluorophenyl)-3-isobutyl-2-cyclopenten-1-one oxime 3-isobutyl-2-cyclopenten-1-one was prepared according to a method similar to the STEP 1 used for Example 33 using sec-butyllithium in place of n-butyllithium. The titled compound was then synthesized starting from 3-isobutyl-2-cyclopenten-1-one according to a procedure similar to that employed for Example 33. mp=154-157° C.; $^1$H NMR (CDCl$_3$, 300 MHz): δ 7.22-7.17 (m, 3H), 7.11-7.04 (m, 1H), 2.79 (m, 2H), 2.56 (m, 2H), 2.16 (d, J=7.5 Hz, 2H), 1.93-1.81 (m, 1H), 0.83 (d, J=6.6 Hz, 6H); APCI MS: m/z 248.1 (M+1).

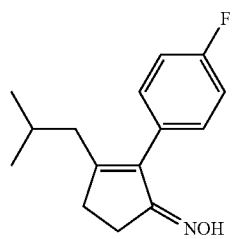

EXAMPLES 86~91

The compounds listed in Table 6 below were prepared according to a procedure similar to that employed for Example 85. The following arylboronic acids were adopted for the Suzuki coupling reaction in STEP 3 in the preparation of Examples 86~90: 3,4-difluorophenylboronic acid for Example 86; 3,4-methylenedioxyphenylboronic acid for Example 87; 3-nitrophenylboronic acid for Example 88; 3-cyanophenylboronic acid for Example 89; 3-fluoro-4-n-nonylphenylboronic acid for Example 90; and 3-n-butoxyphenylboronic acid for Example 91. Spectral data for Examples 86~91 are provided along with their melting points in Table 6.

TABLE 6

Physical characterization data for Examples 86~91.

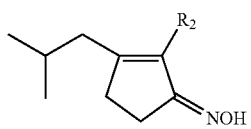

| Example | R$_2$ | Spectral Data | mp, ° C. |
|---|---|---|---|
| 86 | ![3,4-difluorophenyl] | $^1$H NMR (CDCl$_3$, 300 MHz): δ 7.20 (bs, 1H), 7.17 (dt, J=8.4 and 10.5 Hz, 1H), 7.06 (ddd, J=2.1, 7.8 and 11.4 Hz, 1H), 6.95 (m, 1H), 2.79 (m, 2H), 2.56 (m, 2H), 2.16 (d, J=7.5 Hz, 2H), 1.87 (m, 1H), 0.83 (d, J=6.6 Hz, 6H) | 136-139 |
| 87 | ![methylenedioxyphenyl] | $^1$H NMR (CDCl$_3$, 300 MHz): δ 6.93 (bs, 1H), 6.83 (d, J=8.1 Hz, 1H), 6.69 (m, 1H), 5.96 (s, 2H), 2.79 (m, 2H), 2.56 (m, 2H), 2.16 (d, J=7.5 Hz, 2H), 1.87 (m, 1H), 0.83 (d, J=6.6 Hz, 6H) | 168-170 |

TABLE 6-continued

Physical characterization data for Examples 86~91.

[Structure: cyclopentane ring with isobutyl group, R₂ substituent, and =NOH group]

| Example | R₂ | Spectral Data | mp, °C |
|---|---|---|---|
| 88 | [3-nitrophenylmethyl] | ¹H NMR (CDCl₃, 300 MHz): δ 8.17 (dt, J=2.4 and 6.9 Hz, 1H), 8.11 (m, 1H), 7.75 (bs, 1H), 7.56 (m, 2H), 2.80 (m, 2H), 2.62 (m, 2H), 2.17 (d, J=7.5 Hz, 2H), 1.94-1.82 (m, 1H), 0.84 (d, J=6.6 Hz, 6H) | 129-131 |
| 89 | [3-cyanophenylmethyl] | ¹H NMR (CDCl₃, 300 MHz): δ 7.60 (m, 1H), 7.53 (m, 1H), 7.48 (m, 2H), 7.43 (bs, 1H), 2.82 (m, 1H), 2.62 (m, 2H), 2.14 (d, J=7.5 Hz, 2H), 1.88 (hep, J=6.9 Hz, 1H), 0.84 (s, 3H), 0.82 (s, 3H) | 138-140 |
| 90 | [4-fluoro-2-nonylphenylmethyl] | ¹H NMR (CDCl₃, 300 MHz): δ 7.17 (m, 4H), 7.01 (bs, 1H), 2.80 (m, 2H), 2.59 (m, 4H), 2.19 (m, 2H), 1.79 (m, 1H), 1.62 (m, 2H), 1.27 (m, 12H), 0.93 (m, 3H), 0.86 (s, 3H), 0.83 (s, 3H) | 85-86 |
| 91 | [3-butoxyphenylmethyl] | ¹H NMR (CDCl₃, 300 MHz): δ 7.26 (m, 1H), 7.08 (bs, 1H), 6.85-6.75 (m, 3H), 3.95 (t, J=6.6 Hz, 2H), 2.79 (m, 2H), 2.57 (m, 2H), 2.17 (d, J=8.7 Hz, 2H), 1.76 (m, 2H), 1.49 (m, 2H), 0.96 (t, J=7.2 Hz, 3H), 0.84 (s, 3H), 0.82 (s, 3H) | 80-81 |

Biological Evaluation

Compounds of this invention were evaluated for their ability to inhibit the production of TNF-α in stimulated immune cells. $IC_{50}$ values (concentrations for the 50% inhibition of TNF-α production) were read out from dose-response curves. The in vitro inhibition assays were carried out with PDE4 inhibitor rolipram as a positive control. Compounds of the present invention were evaluated for their therapeutic activity in animal models for inflammatory or immunological disorders. Also compounds of this invention were assayed for their ability to inhibit PDE4 isozymes.

Inhibition of TNF-α Production in Rat PBMCs: Compounds of the present invention were evaluated for their ability to inhibit the production of TNF-α in rat peripheral blood mononuclear cells (PBMCs) as described in the literature. [*Exp. Geront.* vol 37, 235-247 (2002)] In brief, 6 ml rat blood drawn from the abdominal vein as treated with ACD (acid/citrate/dextrose) was carefully added in a tube containing 6 ml Ficoll 1077, and the tube was centrifuged for 30 min at 1500 rpm (415 G) at room temperature. The cell fraction (middle fraction) was suspended in a 50 ml tube containing phosphate buffered saline (PBS). The tube was centrifuged for 5 min at 2000 rpm (737 G). The resulting pellet was suspended in 6 ml PBS and 6 ml Ficoll 1077, and centrifuged for 30 min at 1500 rpm (415 G) at room temperature to remove remaining plasma. The cell fraction was suspended in PBS and centrifuged for 5 min at 2000 rpm. Such a washing was repeated twice. Then the collected cells were suspended in 10 ml RPMI-1640 containing 10% FBS and further diluted to contain 4×10⁶ cells per ml. The cell suspension was dispensed into a 96-well plate at 100 µl per well, which was pre-supplemented with 1 µl of either DMSO (placebo) or a DMSO stock solution containing a designated concentration of a compound of this invention. The plate was cultured for an hour at 37° C. under 5% $CO_2$ and 95% $O_2$. To each well, was added 100 µl RPMI-1640 containing 0.1 µg/ml LPS, 5 U/ml IFN-γ, and 10% FBS. Then the plate was subjected to a culture for 18 hours at 37° C. under 5% $CO_2$ and 95% $O_2$. An aliquot of the supernatant from each well was subjected to an ELISA assay to determine the TNF-α level in the well. In Table 7, are summarized observed in vitro activities of compounds of this invention to inhibit the production of TNF-α in rat PBMCs. However, provision of such in vitro inhibitory data is not intended to limit the scope of compounds as provided in Table 7.

TABLE 7

In vitro inhibitory activities of compounds against the production of TNF-α in rat PBMCs.

| Example | $IC_{50}$, µg/ml or % Inhibition | Example | $IC_{50}$, µg/ml or % Inhibition |
|---|---|---|---|
| 1 | 0.12 | 2 | 0.035 |
| 3 | 0.053 | 4 | 0.02 |
| 5 | 66% inhibition @ 0.3 µg/ml | 10 | 0.097 |
| 12 | 0.1 | 13 | 0.4 |
| 18 | 78% inhibition @ 3 µg/ml | 19 | 1 |
| 23 | 1.2 | 25 | 1.5 |
| 27 | 0.34 | 28 | 0.13 |
| 30 | <0.1 | 31 | 0.076 |
| 32 | 0.49 | 33 | 2.0 |
| 34 | 0.3 | 39 | 0.23 |
| 45 | 0.69 | 58 | 59% inhibition @ 3 µg/ml |
| 65 | ~1 | 66 | 1~3 |
| 71 | <1 | 77 | 2.8 |
| 78 | 0.62 | 79 | 0.18 |
| 80 | 0.2 | 81 | ~3 |
| 83 | ~10 | 85 | 0.77 |
| 86 | 0.27 | 89 | 0.09 |
| Rolipram | 0.05~0.1 | | |

Inhibition of TNF-α Production in Human PBMCs: Compounds of the present invention were evaluated for their ability to inhibit the production of TNF-α in human PBMCs as described in the literature. [*J. Med. Chem*. vol 39, 3238-3240 (1996)] Blood was freshly drawn from healthy human subjects as treated with ACD to isolate human PBMCs according to the procedure employed for rat PBMCs. The employed assay method for the ELISA against human TNF-α was essentially identical to that for the rat TNF-α ELISA assay. Compounds of this invention showed comparable inhibitory activities in human and rat PBMCs. In Table 8, are summarized in vitro inhibitory activities in human PBMCs for some compounds of the present invention.

TABLE 8

In vitro inhibitory activities of compounds against the production of TNF-α in human PBMCs.

| Example | IC$_{50}$, μg/ml | Example | IC$_{50}$, μg/ml |
|---|---|---|---|
| 2 | 0.072 | 4 | 0.07 |
| 12 | 0.16 | 45 | 0.8 |
| 65 | 1.2 | Rolipram | 0.01~0.1 |

In vivo Inhibition of TNF-α Production: Compounds of this invention were evaluated for their ability to inhibit in the vivo production of TNF-α in mice upon stimulation with LPS according to a procedure similar to that described in the literature. [*J. Pharmacol. Exp. Therapeut*. vol 279, 1453-1461 (1996)] In brief, either a compound of the instant invention with vehicle or vehicle only (5% Tween 80) was administered by oral gavage (10 ml/kg body weight) at hour 0 to mice (Balb/C or ICR, 25~30 g) fasted overnight. The mice were subjected to a peritoneal injection with 100 mg LPS per mouse at hour 0.5, and blood was drawn from the abdominal vein at hour 2 following euthanasia with $CO_2$. Then plasma separated from the drawn blood by centrifugation was subjected to an ELISA assay to measure the level of TNF-α. The % inhibition of in vivo TNF-α production by a compound of this invention was determined by comparing the observed average TNF-α level in mice received the compound with that in mice received vehicle only. As provided in Table 9, compounds of the present invention potently and effectively inhibited the in vivo production of TNF-α in mice stimulated with LPS, paralleling their in vitro inhibitory activities against TNF-α production.

TABLE 9

In vivo inhibitory activities of compounds against the production of TNF-α in mice stimulated with LPS (n = 5 to 6 per group).

| Example | % Inhibition @ dose | Example | % Inhibition @ dose |
|---|---|---|---|
| 1 | 72% @ 3 mg/kg | 2 | 78% @ 0.3 mg/kg |
| 4 | 63% @ 0.01 mg/kg | 13 | 70% @ 0.3 mg/kg |
| 27 | 87% @ 3 mg/kg | 28 | 88% @ 3 mg/kg |
| 31 | 80% @ 3 mg/kg | 32 | 92% @ 3 mg/kg |
| 39 | 96% @ 3 mg/kg | 45 | 42% @ 1 mg/kg |
| 66 | 45% @ 3 mg/kg | 79 | 85% @ 3 mg/kg |
| 80 | 95% @ 3 mg/kg | Rolipram | ~50% @ 0.2 mg/kg |

Therapeutic Effect in Delayed Type Hypersensitivity: Compounds of this invention were evaluated for their ability to treat inflammation in a mouse model for delayed type hypersensitivity (DTH) according to the literature. [*J. Immunol*. vol 171, 3010 (2003)] In brief, Balb/c mice were shaved in the abdomen and topically administered in the abdominal skin on day 0 with 2% oxazolone dissolved in 9:1 acetone/DMSO (vehicle). On day 5, DTH was elicited by topically administering on the left ear 2% oxazolone. A compound of this invention dissolved in the vehicle was topically applied on the left ear twice firstly at 2 hours before and secondly 4 hours after the elicitation with oxazolone. The therapeutic effect was scored 24 hours after the oxazolone elicitation by comparing the weights of the left (inflamed) and the right (un-inflamed) ears as punched. For example, 37% inhibition of the ear edema was observed for the 3% solution of Example 4 (p<0.05), while 76% inhibition was observed for cyclosporin orally administered twice on day 5 at 90 mg/kg per dose (p<0.01). Five animals per group were evaluated.

Therapeutic Effect in DSS-induced Colitis: Compounds of the present invention were evaluated for their ability to treat colitis induced by dextran sulfate sodium (DSS) in mice according to the literature. [*J. Pharmacol. Exp. Therapeut*. vol. 292, 22-30 (2000)] In brief, female Balb/c mice weighing 16-20 g were randomized into groups (5~6 per group) and were allowed from day 1 free access to water containing 5% DSS. A compound of this invention or sulfasalazine in 5% Tween 80 at 10 ml/kg was orally administered twice a day. Clinical activity score of each animal was measured on a daily basis by evaluating the stool consistency, body weight and rectal bleeding. Therapeutic effect was observed for compounds of this invention. For instance, the animals received Example 4 at 1 mg/kg BID showed on day 11 an improvement of 43% in the clinical score activity (p<0.05) from the control group (vehicle & DSS only), while 19% improvement was observed with animals received sulfasalazine at 50 mg/kg BID (p>0.05).

In vitro Inhibition of cAMP Degradation in U937 Cells: Compounds of this invention were evaluated for their ability to inhibit in cells the hydrolysis of cAMP induced by forskolin, an adenylate cyclase stimulator. In brief, $3\times10^5$ U937 cells per well on a 96-well plate were incubated for 10 min at 37° C. in 200 μl RPMI-1640 containing 10% FBS, which was followed by treatment of either DMSO or a DMSO stock solution of a compound of the present invention at a designated dose. Then the cells were stimulated with 10 μM forskolin for 10 min at 37° C. The plate was centrifuged for 5 min at 1500 rpm. 120 μl of the supernatant was carefully removed from each well and 200 μl of lysis agent 1B was added to the well. Then the cell lysate was assayed to determine the level of cAMP by enzyme immunoassay (EIA) using a cAMP EIA kit from Amersham Pharmacia Biotech (Kit #RPN225). IC$_{50}$'s were determined for compounds of this invention from dose response curves for cAMP levels. Compounds of the present invention potently inhibited the cellular degradation of cAMP in U937 cells. For example, the observed IC$_{50}$ values were 0.1 μg/ml for Example 2, 0.13 μg/ml for Example 4, and 0.87 μg/ml for Example 45, while IC$_{50}$ value of known PDE4 inhibitor rolipram was 0.27 μg/ml.

Inhibition of PDE4 Isozymes: Compounds of the instant invention were evaluated for their ability to inhibit isozymes of phosphodiesterase 4 (PDE4) obtained from Fab Gennix International Inc. (Frisco, Tex./USA) according to a literature method. [*Biochemistry* vol 39, 6449-6458 (2000)] In brief, a compound at a designated dose was assayed for their ability to inhibit the hydrolysis of cAMP by a PDE4 isozyme in pH 7.4 Tris buffer. The resulting level of cAMP was determined by the scintillation proximity assay (SPA) using a SPA kit from Amersham Biosciences according to the supplier's instruction manual (TRKQ7090 Phosphodiesterase [$^3$H]cAMP SPA enzyme assay). Compounds of this invention potently inhibited isozymes of PDE4 as exemplified in Table 10 for some compounds of the present invention.

TABLE 10

Inhibitory activities of compounds against human PDE4 isozymes.

| Example | % Inhibition | |
|---|---|---|
| | PDE4A @ 0.5 µg/ml | PDE4D @ 0.1 µg/ml |
| 1 | 72% | 79% |
| 3 | 89% | 78% |
| 4 | 69% | 59% |
| 10 | 33% | 38% |
| 28 | 58% | 87% |
| 31 | 60% | 59% |
| 79 | 0% | 23% |
| Rolipram | 19% @ 1 µg/ml | 54% |

The invention claimed is:

1. A compound represented by Formula I provided below, or a pharmaceutically acceptable salt thereof:

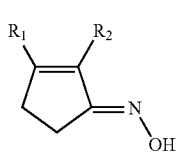

Formula I wherein,
$R_1$ represents a linear or branched $C_1$-$C_{10}$ alkyl group, or a $C_3$-$C_7$ cycloalkyl group; and
$R_2$ represents an aromatic group selected from the group consisting of phenyl, pyridyl, naphthyl, indolyl, thienyl, benzo[b]thienyl, dibenzofuranyl, and thianthrenyl, wherein said phenyl is unsubstituted or substituted by:
one to three substituent(s) selected from the group consisting of a linear $C_1$-$C_9$ alkyl group, phenyl, halo, nitro, alkoxy, cyano and hydroxy, or
one substituent selected from the group consisting of alkenyl, haloalkyl, amino, alkylamino, alkylaminoalkyl, methylenedioxy, haloalkoxy, benzyloxy, alkylthio, alkylsulfonyl, alkylsulfinyl, alkoxycarbonyl, alkoxyalkyl, hydroxyalkyl, carbamoyl, N-hydroxy-iminoalkyl and N-(N-hydroxy-iminoalkyl).

2. A compound according to claim 1 or a pharmaceutically acceptable salt thereof wherein,
$R_1$ represents a linear or branched $C_1$-$C_6$ alkyl, cyclopentyl, or cyclohexyl.

3. A compound according to claim 2 or a pharmaceutically acceptable salt thereof, wherein the compound is selected from the group consisting of:
3-cyclopentyl-2-(4-fluorophenyl)-2-cyclopenten-1-one oxime;
3-cyclopentyl-2-(3,4-difluorophenyl)-2-cyclopenten-1-one oxime;
2-(3-chloro-4-fluorophenyl)-3-cyclopentyl-2-cyclopenten-1-one oxime;
3-cyclopentyl-2-(3-nitrophenyl)-2-cyclopenten-1-one oxime;
3-cyclopentyl-2-(4-methyl-3-nitrophenyl)-2-cyclopenten-1-one oxime;
3-cyclopentyl-2-(3,4-dimethoxyphenyl)-2-cyclopenten-1-one oxime;
3-cyclopentyl-2-(3-methoxyphenyl)-2-cyclopenten-1-one oxime;
3-cyclopentyl-2-{4-methoxy-3-(methoxymethyl)phenyl}-2-cyclopenten-1-one oxime;
2-{4-(benzyloxy)phenyl}-3-cyclopentyl-2-cyclopenten-1-one oxime;
3-cyclopentyl-2-(3,4-methylenedioxyphenyl)-2-cyclopenten-1-one oxime;
3-cyclopentyl-2-{3-(trifluoromethoxy)phenyl}-2-cyclopenten-1-one oxime;
2-(3-cyanophenyl)-3-cyclopentyl-2-cyclopenten-1-one oxime;
2-(3-cyano-4-fluorophenyl)-3-cyclopentyl-2-cyclopenten-1-one oxime;
3-cyclopenty-2-{3-(N,N-dimethylaminomethyl)phenyl}-2-cyclopenten-1-one oxime;
3-cyclopentyl-2-{3-(N,N-dimethylamino)phenyl}-2-cyclopenten-1-one oxime;
3-cyclopentyl-2-{5-(1H)-indolyl}-2-cyclopenten-1-one oxime;
3-cyclopentyl-2-(6-methoxynaphthyl)-2-cyclopenten-1-one oxime;
3-cyclopentyl-2-(4-vinylphenyl)-2-cyclopenten-1-one oxime;
3-cyclopentyl-2-(4-dibenzofuranyl)-2-cyclopenten-1-one oxime;
3-cyclopentyl-2-(2-thianthrenyl)-2-cyclopenten-1-one oxime;
3-cyclopentyl-2-(3-carbamoylphenyl)-2-cyclopenten-1-one oxime;
3-cyclopentyl-2-{3-(methylthio)phenyl}-2-cyclopenten-1-one oxime;
3-cyclopentyl-2-{3-(methylsulfonyl)phenyl}-2-cyclopenten-1-one oxime;
3-cyclopentyl-2-(3-hydroxyphenyl)-2-cyclopenten-1-one oxime;
3-cyclopentyl-2-{3-(hydroxymethyl)phenyl}-2-cyclopenten-1-one oxime;
3-cyclopentyl-2~{4-(hydroxymethyl)phenyl}-2-cyclopenten-1-one oxime;
3-cyclohexyl-2-(4-fluorophenyl)-2-cyclopenten-1-one oxime;
2-(3-chloro-4-fluorophenyl)-3-cyclohexyl-2-cyclopenten-1-one oxime;
3-cyclohexyl-2-(3-fluorophenyl)-2-cyclopenten-1-one oxime;
3-cyclohexyl-2-(3,4-difluorophenyl)-2-cyclopenten-1-one oxime;
3-cyclohexyl-2-(3-nitrophenyl)-2-cyclopenten-1-one oxime;
3-cyclohexyl-2-(3-methoxyphenyl)-2-cyclopenten-1-one oxime;
3-butyl-2-(4-fluorophenyl)-2-cyclopenten-1-one oxime;
3-butyl-2-(3,4-difluorophenyl)-2-cyclopenten-1-one oxime;
3-butyl-2-(2-fluorophenyl)-2-cyclopenten-1-one oxime;
3-butyl-2-(2,4-difluorophenyl)-2-cyclopenten-1-one oxime;
2-(3-bromophenyl)-3-butyl-2-cyclopenten-1-one oxime;
3-butyl-2-(3,4-dichlorophenyl)-2-cyclopenten-1-one oxime;
3-butyl-2-(3-nitrophenyl)-2-cyclopenten-1-one oxime;
3-butyl-2-(3-fluoro-4-methoxyphenyl)-2-cyclopenten-1-one oxime;
3-butyl-2-(3-fluoro-4-hydroxyphenyl)-2-cyclopenten-1-one oxime;
3-butyl-2-(3-ethoxyphenyl)-2-cyclopenten-1-one oxime;
3-butyl-2-(3,4-dimethoxyphenyl)-2-cyclopenten-1-one oxime;
3-butyl-2-(3-methoxyphenyl)-2-cyclopenten-1-one oxime;

3-butyl-2-(3,4-methylenedioxyphenyl)-2-cyclopenten-1-one oxime;
3-butyl-2-{4-(trifluoromethoxy)phenyl}-2-cyclopenten-1-one oxime;
3-butyl-2-{3-(hydroxymethyl)phenyl}-2-cyclopenten-1-one oxime;
3-butyl-2-(3,4-dihydroxyphenyl)-2-cyclopenten-1-one oxime;
3-butyl-2-(3-hydroxyphenyl)-2-cyclopenten-1-one oxime;
2-(3-aminophenyl)-3-butyl-2-cyclopenten-1-one oxime;
3-butyl-2-{3~(ethoxycarbony)phenyl}-2-cyclopenten-1-one oxime;
3-butyl-2-(3-carboxyphenyl)-2-cyclopenten-1-one oxime;
3-butyl-2-(4-carboxyphenyl)-2-cyclopenten-1-one oxime;
3-butyl-2-(3,4-dimethylphenyl)-2-cyclopenten-1-one oxime;
3-butyl-2-(3-methylphenyl)-2-cyclopenten-1-one oxime;
3-butyl-2-(4-butylphenyl)-2-cyclopenten-1-one oxime;
3-butyl-2-(3-fluoro-4-phenylphenyl)-2-cyclopenten-1-one oxime;
3-butyl-2-{3-(trifluoromethyl)phenyl}-2-cyclopenten-1-one oxime;
3-butyl-2-{4-(methanesulfinyl)phenyl}-2-cyclopenten-1-one oxime;
3-butyl-2-{4-(methanesulfonyl)phenyl}-2-cyclopenten-1-one oxime;
3-butyl-2-{3-(N-hydroxyacetimidoyl)aminophenyl}-2-cyclopenten-1-one oxime;
3-butyl-2-{3-(1-N-hydroxyiminoethyl)phenyl}-2-cyclopenten-1-one oxime;
3-butyl-2-{3-(N-hydroxyiminomethyl)phenyl}-2-cyclopenten-1-one oxime;
2-(2-benzo[b]thienyl)-3-butyl-2-cyclopenten-1-one oxime;
3-pentyl-2-phenyl-2-cyclopenten-1-one oxime;
2-(4-fluorophenyl)-3-pentyl-2-cyclopenten-1-one oxime;
2-(3-fluorophenyl)-3-pentyl-2-cyclopenten-1-one oxime;
2-(3,4-difluorophenyl)-3-pentyl-2-cyclopenten-1-one oxime;
2-(3,5-difluorophenyl)-3-pentyl-2-cyclopenten-1-one oxime;
2-(3-chloro-4-fluorophenyl)-3-pentyl-2-cyclopenten-1-one oxime;
2-(3-nitrophenyl)-3-pentyl-2-cyclopenten-1-one oxime;
3-pentyl-2-(3,4,5-trimethoxyphenyl)-2-cyclopenten-1-one oxime;
2-(4-biphenyl)-3-pentyl-2-cyclopenten-1-one oxime;
3-pentyl-2-{4-(trifluoromethyl)phenyl}-2-cyclopenten-1-one oxime;
2-(1-naphthyl)-3-pentyl-2-cyclopenten-1-one oxime;
3-pentyl-2-(3-pyridyl)-2-cyclopenten-1-one oxime;
3-pentyl-2-(3-thienyl)-2-cyclopenten-1-one oxime;
2-(4-fluorophenyl)-3-propyl-2-cyclopenten-1-one oxime;
2-(3,4-difluorophenyl)-3-propyl-2-cyclopenten-1-one oxime;
2-(3-nitrophenyl)-3-propyl-2-cyclopenten-1-one oxime;
3-ethyl-2-(4-fluorophenyl)-2-cyclopenten-1-one oxime;
2-(3,4-difluorophenyl)-3-ethyl-2-cyclopenten-1-one oxime;
2-(4-fluorophenyl)-3-methyl-2-cyclopenten-1-one oxime;
2-(3,4-difluorophenyl)-3-methyl-2-cyclopenten-1-one oxime;
2-(4-fluorophenyl)-3-isobutyl-2-cyclopenten-1-one oxime;
2-(3,4-difluorophenyl)-3-isobutyl-2~cyclopenten-1-one oxime;
2-(3,4-methylenedioxyphenyl)-3-isobutyl-2-cyclopenten-1-one oxime;
3-isobutyl-2-(3-nitrophenyl)-2-cyclopenten-1-one oxime;
2-(3-cyanophenyl)-3-isobutyl-2-cyclopenten-1-one oxime;
2-(3-fluoro-4-n-nonylphenyl)-3-isobutyl-2-cyclopenten-1-one oxime; and
2-(3-butoxyphenyl)-3-isobutyl-2-cyclopenten-1-one oxime.

4. A pharmaceutical composition comprising a therapeutically effective amount of a compound of claim 1 or a pharmaceutically acceptable salt thereof as an active ingredient and a pharmaceutically acceptable adjuvant.

5. A pharmaceutical composition according to claim 4, for treating a TNF-α mediated disease, said TNF-α mediated disease being inflammatory or immunological disorder.

6. A pharmaceutical composition according to claim 4, for treating a TNF-α mediated disease, said TNF-α mediated disease being selected from the group consisting of: rheumatoid arthritis, psoriasis, psoriatic arthritis, atopic dermatitis, inflammatory bowel disease including ulcerative colitis and Crohn's disease, ankylosing spondylitis, multiple sclerosis, systemic lupus erythematosus (SLE), chronic obstructive pulmonary disease (COPD), sepsis, endotoxin shock, hepatitis, and Type I diabetes.

7. A pharmaceutical composition according to claim 4, for treating a TNF-α mediated disease, said TNF-α mediated disease being inflammatory bowel disease including ulcerative colitis and Crohn's disease, psoriasis, or atopic dermatitis.

8. A pharmaceutical composition according to claim 4, for treating a PDE4 mediated disease, said PDE4 mediated disease being asthma or chronic obstructive pulmonary disease (COPD).

9. A method for treating a disease selected from the group consisting of: rheumatoid arthritis, psoriatic arthritis, atopic dermatitis, inflammatory bowel disease including ulcerative colitis and Crohn's disease, ankylosing spondylitis, multiple sclerosis, systemic lupus erythematosus (SLE), chronic obstructive pulmonary disease (COPD), endotoxin shock, and Type I diabetes, comprising administering to a subject in need thereof a therapeutically effective amount of the compound of claim 1 or a pharmaceutically acceptable salt thereof.

10. A method according to claim 9, wherein the disease is inflammatory bowel disease including ulcerative colitis and Crohn's disease, or atopic dermatitis.

* * * * *